US008728525B2

(12) United States Patent
Brown et al.

(10) Patent No.: US 8,728,525 B2
(45) Date of Patent: *May 20, 2014

(54) PROTEIN MICROSPHERES RETAINING PHARMACOKINETIC AND PHARMACODYNAMIC PROPERTIES

(75) Inventors: Larry R. Brown, Newton, MA (US); Mark X. Yang, Newton, MA (US); Ed O'Connell, Brighton, MA (US)

(73) Assignees: Baxter International Inc., Deerfield, IL (US); Baxter Healthcare SA, Glattpark (Opfikon) (CH)

( * ) Notice: Subject to any disclaimer, the term of this patent is extended or adjusted under 35 U.S.C. 154(b) by 1431 days.

This patent is subject to a terminal disclaimer.

(21) Appl. No.: 11/557,486

(22) Filed: Nov. 7, 2006

(65) Prior Publication Data

US 2007/0207210 A1    Sep. 6, 2007

Related U.S. Application Data

(63) Continuation-in-part of application No. 11/127,704, filed on May 12, 2005, now Pat. No. 8,333,995, which is a continuation of application No. 10/894,410, filed on Jul. 19, 2004, now abandoned.

(60) Provisional application No. 60/570,274, filed on May 12, 2004.

(51) Int. Cl.
*A61K 9/19* (2006.01)
*A61K 9/10* (2006.01)

(52) U.S. Cl.
USPC ........... 424/489; 424/130.1; 514/5.9; 514/6.8

(58) Field of Classification Search
None
See application file for complete search history.

(56) References Cited

U.S. PATENT DOCUMENTS

| | | | |
|---|---|---|---|
| 3,737,337 A | 6/1973 | Schnoring et al. | |
| 3,891,570 A | 6/1975 | Fukushima et al. | |
| 4,389,330 A | 6/1983 | Tice et al. | |
| 4,530,840 A | 7/1985 | Tice et al. | |
| 4,584,894 A | 4/1986 | Fogelberg | |
| 4,652,441 A | 3/1987 | Okada et al. | |
| 4,728,721 A | 3/1988 | Yamamoto et al. | |
| 4,818,542 A | 4/1989 | DeLuca et al. | |
| 4,849,228 A | 7/1989 | Yamamoto et al. | |
| 4,861,627 A | 8/1989 | Mathiowitz et al. | |
| 4,897,268 A | 1/1990 | Tice et al. | |
| 4,904,479 A | 2/1990 | Illum | |
| 4,917,893 A | 4/1990 | Okada et al. | |
| 5,075,109 A | 12/1991 | Tice et al. | |
| 5,102,872 A | 4/1992 | Singh et al. | |
| 5,149,543 A | 9/1992 | Cohen et al. | |
| 5,213,812 A | 5/1993 | Ruiz | |
| 5,300,464 A | 4/1994 | Rittler | |
| 5,330,767 A | 7/1994 | Yamamoto et al. | |
| 5,330,768 A | 7/1994 | Park et al. | |
| 5,360,610 A | 11/1994 | Tice et al. | |
| 5,384,133 A | 1/1995 | Boyes et al. | |
| 5,407,609 A | 4/1995 | Tice et al. | |
| 5,417,986 A | 5/1995 | Reid et al. | |
| 5,422,120 A | 6/1995 | Kim | |
| 5,476,663 A | 12/1995 | Okada et al. | |
| 5,480,656 A | 1/1996 | Okada et al. | |
| 5,482,927 A | 1/1996 | Maniar et al. | |
| 5,525,519 A | 6/1996 | Woiszwillo | |
| 5,543,158 A | 8/1996 | Gref et al. | |
| 5,554,730 A | 9/1996 | Woiszwillo et al. | |
| 5,556,642 A | 9/1996 | Kobayashi et al. | |
| 5,575,987 A | 11/1996 | Kamei et al. | |
| 5,578,709 A * | 11/1996 | Woiszwillo | 530/410 |
| 5,599,719 A | 2/1997 | Woiszwillo | |
| 5,603,961 A | 2/1997 | Suzuki et al. | |
| 5,620,883 A | 4/1997 | Shao et al. | |
| 5,631,020 A | 5/1997 | Okada et al. | |
| 5,631,021 A | 5/1997 | Okada et al. | |
| 5,643,607 A | 7/1997 | Okada et al. | |
| 5,650,173 A | 7/1997 | Ramstack et al. | |
| 5,654,008 A | 8/1997 | Herbert et al. | |
| 5,654,010 A | 8/1997 | Johnson et al. | |
| 5,665,428 A | 9/1997 | Cha et al. | |
| 5,667,808 A | 9/1997 | Johnson et al. | |

(Continued)

FOREIGN PATENT DOCUMENTS

| | | |
|---|---|---|
| CA | 2157793 A1 | 9/1994 |
| DE | 4312970 | 10/1994 |
| DE | 19812083 | 9/1999 |
| DE | 10157799 | 9/2002 |
| EP | 248531 A2 | 1/1986 |
| EP | 248531 A3 | 1/1986 |
| EP | 0377477 | 7/1990 |
| EP | 0564061 B1 | 10/1993 |
| EP | 0647477 | 4/1995 |
| EP | 809110 A1 | 11/1997 |

(Continued)

OTHER PUBLICATIONS

Falkenberg J. Clin. Chem. Biochem. 1984, 22:867-882).*

(Continued)

*Primary Examiner* — Sharon Wen
(74) *Attorney, Agent, or Firm* — Marshall, Gerstein & Borun LLP

(57) ABSTRACT

The present disclosure relates to compositions of methods of making and compositions small compositions of particles of an active agent. In accordance with the method of production, the active agent is dissolved in an aqueous or aqueous-miscible solvent containing a dissolved phase-separation enhancing agent (PSEA) to form a solution in a single liquid phase. The solution is subjected to a liquid-solid phase separation to cause the active agent to form small spherical particles that are substantially amorphous or non-crystalline and are injectable through fine bore needles at high concentrations. The particles exhibit the pharmacokinetic and pharmacodynamnic properties of the active agent. The disclosure has special application for higher molecular weight proteins such as antibodies.

55 Claims, 23 Drawing Sheets

(56) References Cited

U.S. PATENT DOCUMENTS

| | | |
|---|---|---|
| 5,716,640 A | 2/1998 | Kamei et al. |
| 5,851,451 A | 12/1998 | Takechi et al. |
| 5,858,973 A | 1/1999 | Habener et al. |
| 5,891,478 A | 4/1999 | Johnson et al. |
| 5,932,248 A | 8/1999 | Chen et al. |
| 5,945,126 A | 8/1999 | Thanoo et al. |
| 5,972,707 A | 10/1999 | Roy et al. |
| 5,981,719 A | 11/1999 | Woiszwillo et al. |
| 5,989,463 A | 11/1999 | Tracy et al. |
| 6,020,175 A | 2/2000 | Onda et al. |
| 6,036,976 A | 3/2000 | Takechi et al. |
| 6,048,550 A | 4/2000 | Chan et al. |
| 6,051,259 A | 4/2000 | Johnson et al. |
| 6,063,910 A | 5/2000 | Debenedetti |
| 6,090,925 A | 7/2000 | Woiszwillo et al. |
| 6,107,084 A | 8/2000 | Onda et al. |
| 6,120,787 A | 9/2000 | Gustafsson et al. |
| 6,140,475 A | 10/2000 | Margolin et al. |
| 6,153,211 A | 11/2000 | Hubbell et al. |
| 6,242,230 B1 | 6/2001 | Batich et al. |
| 6,252,055 B1 | 6/2001 | Relton et al. |
| 6,265,389 B1 | 7/2001 | Burke |
| 6,267,958 B1 | 7/2001 | Andya et al. |
| 6,268,053 B1 | 7/2001 | Woiszwillo et al. |
| 6,270,795 B1 | 8/2001 | Jones et al. |
| 6,270,802 B1 | 8/2001 | Thanoo et al. |
| 6,312,727 B1 | 11/2001 | Schacht et al. |
| 6,361,798 B1 | 3/2002 | Thanoo et al. |
| 6,395,253 B2 | 5/2002 | Levy et al. |
| 6,395,302 B1 | 5/2002 | Hennink et al. |
| 6,455,074 B1 | 9/2002 | Tracy et al. |
| RE37,872 E | 10/2002 | Franks et al. |
| 6,458,387 B1 | 10/2002 | Scott et al. |
| 6,475,995 B1 | 11/2002 | Roy et al. |
| 6,479,146 B1 | 11/2002 | Caruso et al. |
| 6,500,448 B1 | 12/2002 | Johnson et al. |
| 6,506,410 B1 | 1/2003 | Park et al. |
| 6,541,606 B2 | 4/2003 | Margolin et al. |
| 6,569,458 B1 | 5/2003 | Gombotz et al. |
| 6,596,316 B2 | 7/2003 | Lyons et al. |
| 6,616,949 B2 | 9/2003 | Jonsson et al. |
| 6,630,169 B1 | 10/2003 | Bot et al. |
| 6,645,525 B1 | 11/2003 | Woiszwillo |
| RE38,385 E | 1/2004 | Franks et al. |
| 6,699,501 B1 | 3/2004 | Neu et al. |
| 6,713,533 B1 | 3/2004 | Panzner et al. |
| 6,749,866 B2 | 6/2004 | Bernstein et al. |
| 6,814,980 B2 | 11/2004 | Levy et al. |
| 6,830,737 B2 | 12/2004 | Ramstack |
| 6,833,192 B1 | 12/2004 | Caruso et al. |
| 6,849,259 B2 | 2/2005 | Haurum et al. |
| 6,861,064 B1 | 3/2005 | Laakso et al. |
| 6,862,890 B2 | 3/2005 | Williams et al. |
| 6,875,432 B2 | 4/2005 | Liu et al. |
| 6,974,593 B2 | 12/2005 | Henriksen et al. |
| 6,998,393 B2 | 2/2006 | Jin et al. |
| 7,129,222 B2 | 10/2006 | Van Nest et al. |
| 2001/0002261 A1 | 5/2001 | Morrison et al. |
| 2002/0009453 A1 | 1/2002 | Haurum et al. |
| 2002/0045571 A1 | 4/2002 | Liu et al. |
| 2002/0136719 A1 | 9/2002 | Shenoy et al. |
| 2002/0137156 A1 | 9/2002 | Margolin et al. |
| 2002/0146459 A1 | 10/2002 | Levy et al. |
| 2002/0187197 A1 | 12/2002 | Caruso et al. |
| 2002/0197325 A1 | 12/2002 | Osborne |
| 2003/0007990 A1 | 1/2003 | Blankenship et al. |
| 2003/0026844 A1 | 2/2003 | Lee et al. |
| 2003/0059474 A1 | 3/2003 | Scott et al. |
| 2003/0124368 A1 | 7/2003 | Lynn et al. |
| 2003/0129239 A1 | 7/2003 | Goldshtein |
| 2003/0137067 A1 | 7/2003 | Cooper et al. |
| 2003/0157181 A1 | 8/2003 | Panzner et al. |
| 2003/0175239 A1 | 9/2003 | Margolin et al. |
| 2003/0180370 A1 | 9/2003 | Lesniak et al. |
| 2003/0211153 A1 | 11/2003 | Johnson et al. |
| 2003/0219384 A1 | 11/2003 | Donath et al. |
| 2003/0236214 A1 | 12/2003 | Wolff et al. |
| 2004/0013721 A1 | 1/2004 | Antipov et al. |
| 2004/0013738 A1 | 1/2004 | Voigt et al. |
| 2004/0014698 A1 | 1/2004 | Hortelano et al. |
| 2004/0017018 A1 | 1/2004 | Pommersheim |
| 2004/0043076 A1 | 3/2004 | Dulieu et al. |
| 2004/0047979 A1 | 3/2004 | Qiu et al. |
| 2004/0110898 A1 | 6/2004 | Dreja et al. |
| 2004/0185091 A1 | 9/2004 | Truong et al. |
| 2004/0197324 A1 | 10/2004 | Liu et al. |
| 2004/0202643 A1 | 10/2004 | Margolin et al. |
| 2004/0209804 A1 | 10/2004 | Govardhan et al. |
| 2004/0219224 A1 | 11/2004 | Yakovlevsky et al. |
| 2004/0241202 A1 | 12/2004 | Chluba et al. |
| 2004/0258762 A1 | 12/2004 | Boppart et al. |
| 2005/0048127 A1 | 3/2005 | Brown et al. |
| 2005/0053666 A1 | 3/2005 | Tzannis et al. |
| 2005/0142201 A1 | 6/2005 | Rashba-Step et al. |
| 2005/0142205 A1 | 6/2005 | Rashba-Step et al. |
| 2005/0142206 A1 | 6/2005 | Brown et al. |
| 2005/0147687 A1 | 7/2005 | Rashba-Step et al. |
| 2005/0158303 A1 | 7/2005 | Liu et al. |
| 2005/0170005 A1 | 8/2005 | Rashba-Step et al. |
| 2005/0175603 A1 | 8/2005 | Liu et al. |
| 2005/0180967 A1 | 8/2005 | Haurum et al. |
| 2005/0202072 A1 | 9/2005 | Buch-Rasmussen et al. |
| 2005/0233945 A1 | 10/2005 | Brown et al. |
| 2005/0271731 A1 | 12/2005 | Suzuki et al. |
| 2006/0002862 A1 | 1/2006 | Truong-Le et al. |
| 2006/0018971 A1 | 1/2006 | Scott et al. |
| 2006/0024240 A1 | 2/2006 | Brown et al. |
| 2006/0024379 A1 | 2/2006 | Brown et al. |
| 2006/0127395 A1 | 6/2006 | Arvinte et al. |
| 2006/0182740 A1 | 8/2006 | Yang et al. |
| 2007/0023776 A1 | 2/2007 | Zakgeym et al. |
| 2007/0065440 A1 | 3/2007 | Tomlinson et al. |
| 2007/0122411 A1 | 5/2007 | Matheus et al. |
| 2007/0172475 A1 | 7/2007 | Matheus et al. |
| 2007/0172479 A1 | 7/2007 | Warne et al. |

FOREIGN PATENT DOCUMENTS

| | | |
|---|---|---|
| EP | 0972563 | 1/2000 |
| EP | 1060741 A1 | 12/2000 |
| EP | 1116516 | 7/2001 |
| EP | 1173151 B1 | 1/2002 |
| EP | 1283720 B1 | 2/2003 |
| EP | 1801123 A2 | 6/2004 |
| EP | 0907378 B1 | 2/2006 |
| JP | 08245815 | 9/1996 |
| JP | 2006219455 | 8/2006 |
| WO | WO-93/14110 | 7/1993 |
| WO | 2157793 C | 9/1994 |
| WO | WO-94/18947 | 9/1994 |
| WO | WO 94/20856 | 9/1994 |
| WO | WO-94/24263 | 10/1994 |
| WO | WO/9500128 | 5/1995 |
| WO | WO-96/03978 | 2/1996 |
| WO | WO-96/08289 | 3/1996 |
| WO | WO-97/45140 | 12/1997 |
| WO | WO-99/47252 | 9/1999 |
| WO | WO-99/47253 | 9/1999 |
| WO | WO-00/03797 | 1/2000 |
| WO | WO-00/28972 | 5/2000 |
| WO | WO-00/41679 | 7/2000 |
| WO | WO-00/62759 | 10/2000 |
| WO | WO-00/77281 | 12/2000 |
| WO | WO-01/51196 | 7/2001 |
| WO | WO-01/64330 | 9/2001 |
| WO | WO-01/89563 | 11/2001 |
| WO | WO-02/01788 | 1/2002 |
| WO | WO-02/09865 | 2/2002 |
| WO | WO-02/09864 | 2/2002 |
| WO | WO-02/072636 | 9/2002 |
| WO | WO-02/074431 | 9/2002 |
| WO | WO-02/096457 | 12/2002 |
| WO | WO 03/000014 A2 | 1/2003 |
| WO | WO-03/015750 | 2/2003 |

(56) References Cited

FOREIGN PATENT DOCUMENTS

| | | |
|---|---|---|
| WO | WO-03/030874 | 4/2003 |
| WO | WO-03/043729 | 5/2003 |
| WO | WO-03/087384 | 10/2003 |
| WO | WO-03/090920 | 11/2003 |
| WO | WO-03/097706 | 11/2003 |
| WO | WO-2004/001007 | 12/2003 |
| WO | WO-2004/030649 | 4/2004 |
| WO | WO-2004/058156 | 7/2004 |
| WO | WO-2004/060343 | 7/2004 |
| WO | WO-2004/060920 | 7/2004 |
| WO | WO-2004/100928 | 11/2004 |
| WO | WO-2005/112893 | 2/2005 |
| WO | WO-2005/035088 | 4/2005 |
| WO | WO 2005001355 A1 | 6/2005 |
| WO | WO 2005077414 A1 | 8/2005 |
| WO | WO-2005/089727 | 9/2005 |
| WO | WO-2005/112885 | 12/2005 |
| WO | WO-2005/112894 | 12/2005 |
| WO | WO-2005/123131 | 12/2005 |
| WO | WO-2006/031560 | 3/2006 |
| WO | WO-2006/065746 | 6/2006 |
| WO | WO-2006/112838 | 10/2006 |
| WO | WO-2007/076062 | 7/2007 |

OTHER PUBLICATIONS

Huber Klin. Wochenschr. 1998, 58:1217-1231.*
Ann, C.H, et al , Biodegradable poly(ethylenimine) for plasmid DNA delivery, Journal of Controlled Release, 2002, vol. 80(1-3), pp. 273-282.
Brazeau, G.A., et al., In vitro myotoxicity of selected cationic macromolecules used in non-viral gene delivery, Pharmaceutical Research, 1998, vol. 15(5), pp. 680-684.
Brown, et al , "Pulmonary Delivery of Novel Insulin Microspheres", Proceed, Respiratory Drug Delivery VIII, DHI Publishing, Raleigh, N.C., 2002, pp. 431-434.
Brown, et al , PROMAXX Microsphere Characterization, in Proceed. of Resp. Drug. Del. IX, 2004, pp. 477-479.
Bustami, et al., Generation of micro-particles of proteins for aerosol delivery using high pressure modified carbon dioxide, Pharmaceutical Research, Nov. 2000, vol. 17, No. 11, pp. 1360-1366.
Chu, C.J. , et al., Efficiency of cytoplasmic delivery by pH-sensitive liposomes to cells in culture, Pharm. Res., 1990, vol. 7, pp. 824-834.
Moghimi, "Chemical camouflage of nanospheres with a poorly reactive surface: towards development of stealth and target-specific nanocarriers", Biochimica et Biophysica Acta, vol. 1590, pp. 131-139, 2000.
Morita, et al., Formation and Isolation of Spherical Fine Protein Microparticles Through Lyophilization of Protein-Poly (ethylene Glycol) Aqueous Mixture, Pharmaceutical Research, 2000, vol. 17, No. 11.
Rashba-Step et al., Albumin Microspheres as Drug Delivery Vehicle for Multiple Routes of Administration, Proceed. Int'l. Symp. Control. Rel. Bioact. Materials., 2001, vol. 28.
Sah, H.K., et al ,Biodegradable microcapsules prepared by a w/o/w technique: effects of shear force to make a primary w/o emulsion on their morphology and protein release, J. of Microencapsulation, 1995, vol. 12(1), pp. 59-69.
Sinha, et al., Biodegradable microspheres for protein delivery, Journal of Controlled Release, 2003, vol. 90, pp. 261-280.
Yang, et al., Crystalline monoclonal antibodies for subcutaneous delivery, Proc Natl. Acad. Sci (USA), Jun. 10, 2003, vol. 100, No. 12, pp. 6934-6939.
Zhao, Q , et al., Modulation of oligonucleotide-induced immune stimulation by cyclodextrin analogs.Biochem. Pharmacol., 1996, vol. 52, pp. 1537-1544.
Report of the International Searching Authority PCT/US05/016651 pp. 1-3, Sep. 5, 2005.
Report of the International Searching Authority PCT/US04/23182 pp. 1-3, Nov. 3, 2005.

Opinion of the International Searching Authority PCT/US05/016651 pp. 1-6, Sep. 5, 2005.
Opinion of the International Searching Authority PCT/US04/23182 pp. 1-3, Nov. 3, 2005.
Eliassi et al. Densities of Poly (ethylene glycol) + Water Mixtures in the 298. 15-328 15 K Temperature, Aug. 1998, Journal of Chemical and Engineering Data, vol. 43 pp. 719-721.
Leaversuch, R. Materials: Renewable PLA Polymer Gets 'Green Light' for Packaging Uses, Mar. 2002, Plastics Technology Online at http://www.ptonline.com/articles/200203fa2.html, pp. 1-4.
Al et al., "Nano-encapsulation of furosemide microcrystals for controlled drug release," J. Control. Release, 86:59-68 (2003).
Ariga et al., "Self-assembly of functional protein multilayers: from planar films to microtemplate encapsulation," pp. 367-391, IN: Malmsten (ed.), Biopolymers at Interfaces, 2nd ed., Marcel Dekker (2003).
Banchereau et al., "Dendritic cells and the control of immunity," Nature, 392:245-252 (1998).
Berton et al., "Improved oligonucleotide uptake and stability by a new drug carrier, the supramolecular bio vector (SMBV)," Biochim. Biophys. Acta, 1355:7-19 (1997).
Bisker-Leib et al., "Uniform microsphere formation from small organic molecules," Transactions, 31st Ann. Meeting Control. Release Soc., #631A (2004).
Bisker-Leib et al., "Factor VII monoclonal antibody microspheres," IN: Proc. 2004 Am. Assoc. Pharm. Scientists Natl. Biotech. Conf., p. 76 (2004).
Boussif et al., "A versatile vector for gene and oligonucleotide transfer into cells in culture and in vivo: polyethylenimine," Proc. Natl. Acad. Sci. USA, 92:7297-7301 (1995).
Byrne et al., "Dendritic cells: making progress with tumour regression?" Immunol. Cell Biol., 80:520-530 (2002).
Chamarthy et al., "A cationic peptide consists of ornithine and histidine repeats augments gene transfer in dendritic cells," Mol. Immunol., 40:483-490 (2003).
Check, "A tragic setback," Nature, 420:116-118 (2002).
Chollet et al., "Side-effects of a systemic injection of linear polythylenimine-DNA complexes," J. Gene Med., 41:84-91 (2002).
Couvreur et al., "pH-sensitive liposomes: an intelligent design system for the delivery of antisense oligonucleotides," J. Liposome Res., 7:1-18 (1997).
Crystal, "Transfer of genes to humans: early lessons and obstacles for success," Science, 270:404-410 (1995).
Dokka et al., "Inhibition of endotoxin-induced lung inflammation by interleukin-10 gene transfer in mice," Am. J. Physiol. Lung Cell Mol. Physiol., 279:L872-L877 (2000).
European Patent Office Search Report for EP04809503.8, Aug. 22, 2007.
European Patent Office Search Report for EP04809503.8, Nov. 14, 2007.
European Patent Office Search Report for EP05748256.4, May 8, 2007.
Felgner et al., "Cationic liposome-mediated transfection," Nature, 337:387-388 (1989).
Glorioso et al., "Development of herpes simplex virus vectors for gene transfer to the central nervous system," pp. 281-302, In: Wolff (ed.), Gene Therapeutics: Methods and Applications of Direct Gene Transfer (1993).
Govardhan et al., "Novel long-acting crystal formulation of human growth hormone," Pharm. Res., 22:1461-1470 (2005).
Hudson et al., "Biodegradable polymer matrices for the sustained exogenous delivery of a biologically active c-myc hammerhead ribozymes," Int. J. Pharm., 136:23-29 (1996).
Hughes et al., "Evaluation of adjuvants that enhance the effectiveness of antisense oligodeoxynucleotides," Pharm. Res., 13:404-410 (1996).
Hwang et al., "Cationic polymers for gene delivery: designs for overcoming barriers to systemic administration," Curr. Opin. Mol. Ther., 3:183-191 (2001).
Kabanov et al., "Water-soluble block polycations as carriers for oligonucleotide delivery," Bioconjugate Chem., 6:639-643 (1995).

(56) References Cited

OTHER PUBLICATIONS

Kataoka et al., "Spontaneous formation of polyion complex micelles with narrow distribution from antisense oligonucleotide and cationic block copolymer in physiological saline," *Macromolecules*, 29:8556-8557 (1996).

Larionova et al., "Encapsulation of proteins in polyelectrolyte microcapsules. Factors regulating the protein release," *Proc. Intl. Symp. Control. Release Bioact. Mater.*, 28:1398-1399 (2001).

Legendre, "Delivery of plasmid DNA into mammalian cell lines using pH-sensitive liposomes: comparison with cationic liposomes," *Pharm. Res.*, 9:1235-1242 (1992).

Loke et al., "Delivery of c-myc antisense phosphorothioate oligodeoxynucleotides to hematopoietic cells in culture by liposome fusion: specific reduction in c-myc protein expression correlates with inhibition of cell growth and DNA synthesis," *Curr. Top. Microbiol. Immunol.*, 141:282-289 (1988).

Lvov et al., "Nanoengineered shells for encapsulation and controlled release," pp. 1-3, *NSF Nanoscale Science and Engineering Grantees Conference* (Dec. 16-18, 2003).

Mahato et al., "Cationic lipid-based gene delivery systems: pharmaceutical perspectives," *Pharm. Res.*, 14:853-859 (1997).

Meiri et al., "Reversible antisense inhibition of Shaker-like Kv1.1 potassium channel expression impairs associative memory in mouse and rat," Proc. Natl. Acad. Sci. USA, 94:4430-4434 (1997).

Middaugh, "Oligonucleotide delivery," in: Mathiowitz (ed.), *Encyclopedia of Controlled Drug Delivery*, vol. 2, pp. 691-697, John Wiley & Sons (1999).

Miller, "Human gene therapy comes of age," *Nature*, 357:455-460 (1992).

Oberhouser et al., "Enhancing endosomal exit of nucleic acids using pH-sensitive viral fusion peptides," pp. 247-266, In: Akhatar (ed.), *Delivery Strategies for Antisense Oligonucleotides Therapeutics*, Boca Raton, FL: CRC Press (1995).

Opinion of the Internatioanl Searching Authority, PCT/US05/016660, Dec. 6, 2005.

Opinion of the International Searching Authority, PCT/US05/16689, Nov. 29, 2005.

Opinion of the International Searching Authority, PCT/US2006/015918, Sep. 18, 2006.

Pargaonkar et al., "Controlled release of dexamethasone from microcapsules produced by polelectrolyte layer by layer nanoassembly," *Pharm. Res.*, 22:829-835 (2005).

Perlaky et al., "Growth inhibition of human tumor cell lines by antisense oligonucleotides designed to inhibit p120 expression," *Anti-Cancer Drug Des.*, 8:3-14 (1993).

Pommersheim et al., "Immobilization of enzymes by multilayer microcapsules," *Macromol. Chem. Phys.*, 195:1557-1567 (1994).

Qiu et al., "Studies on the drug release properties of polysaccharide multilayers encapsulated ibuprofen microparticles," *Langmuir*, 17:5375-5380 (2001).

Radler et al., "Structure of DNA-cationic liposome complexes: DNA intercalation in multilamellar membranes in distinct interhelical packing regimes,"*Science*, 275:810-814 (1997).

Rashba-Step et al.,"PROMAXX protein matrix microspheres for delivery of alpha-1 antitrypsin via the pulmonary route," *Transactions 31st Annual Meeting Control. Release Soc.*, #474 (2004).

Report of the International Searching Authority PCT/US04/016660, Dec. 6, 2005.

Report of the International Searching Authority, PCT/US0516689, Nov. 29, 2005.

Report of the International Searching Authority, PCT/US2006/015918, Sep. 18, 2006.

Schwartz et al., "Synthetic DNA-compacting peptides derived from human sequence enhance cationic lipid-mediated gene transfer in vitro and in vivo," *Gene Ther.*, 6:282-292 (1999).

Sukhorukov et al., "Controlling release and permeability properties of militilayer [sic] polyeletrolyte capsules," *Proc. Intl. Symp. Control. Release Bioact. Mater.*, 28:1402-1403 (2001).

Sweeney et al., "Efficient therapeutic gene delivery after systemic administration of a novel polyethylenimine/DNA vector in an orthotopic bladder cancer model," *Cancer Res.*, 63:4017-4020 (2003).

Thierry et al., "Overcoming multidrug resistance in human tumor cells using free and liposomally encapsulated antisense oligodeoxynucleotides," *Biochem. Biophys. Res. Commun.*, 190:952-960 (1993).

Tiourina et al., "Encapsulation of alpha chymotrypsin onto the hollow polyelectrolyte microcapsules," *Proc. Intl. Symp. Control. Release Bioact. Mater.*, 28:1400-1401 (2001).

Tiyaboonchai et al., "Formulation and characterization of DNA-polyethylenimine-dextran sulfate nanoparticles," *Eur. J. Pharm. Sci.*, 19:191-202 (2003).

Tomilnson et al., "Controllable gene therapy: pharmaceutics of non-viral gene delivery systems," *J. Control. Release*, 39:357-372 (1996).

Vanderkerken et al., "Synthesis and evaluation of poly(ethylene glycol)-polylysine block copolymers as carriers for gene delivery," *J. Bioactive Compatible Polymers*, 15:115-138 (2000).

Vanderlubben et al., "Chitosan microparticles for mucosal vaccination against diphtheria: oral and nasal efficacy studies in mice," *Vaccine*, 21:1400-1408 (2003).

Yamakawa et al., "Release behavior of poly(lactic acid-co-glycolic acid) implants containing phosphorothioate oligodeoxynucleotide," *Biol. Pharm. Bull.*, 20:455-459 (1997).

Yang et al., "Layer by layer construction of novel biofunctional fluorescent microparticles for immunoassay applications," *J. Colloid Interface Sci.*, 234:356-362 (2001).

Yang et al., "Novel fluorescent labels prepared by layer to layer assembly on colloids for biodetection systems," *Mat. Res. Soc. Symo. Proc.*, 667:G5.51-G5.5.6 (2001).

Zahr et al., "Fabrication of core-shell drug nonoparticles for therapeutic delivery," *Polymeric Materials: Science and Engineering*, 93:802-803 (2005).

Zelphati et al., "Mechanism of oligonucleotide release from cationic lipids," *Proc. Natl. Acad. Sci. USA*, 100:11493-11498 (1996).

US 5,849,884, 12/1998, Woiszwillo et al. (withdrawn)

\* cited by examiner a b

PROTEIN MICROSPHERES RETAINING PHARMACOKINETIC AND PHARMACODYNAMIC PROPERTIES

CROSS-REFERENCE TO RELATED APPLICATION

This application is a continuation-in-part of application Ser. No. 11/127,704, filed May 12, 2005 now U.S. Pat. No. 8,333,995, which is a continuation-in-part of application Ser. No. 10/894,410, filed Jul. 19, 2004 now abandoned, and claims priority to U.S. Provisional Application Ser. No. 60/570,274 filed May 12, 2004, each of which is incorporated herein in its entirety by reference and made a part hereof.

TECHNICAL FIELD

The present disclosure relates to compositions of small particles, which may be substantially spherical in shape, of an active agent. The active agents may be high molecular weight proteins, and typically are substantially amorphous forms of high molecular weight proteins, including substantially amorphous monoclonal antibodies. The disclosure describes providing injectable or syringeable compositions of high molecular weight proteins, including monoclonal antibodies, at high concentrations, and accordingly provides the ability to deliver a clinically effective dose of such active agents with a low volume of composition, with 10 ml or less of composition, and more typically with a volume typically found in injection syringe applications including syringeable low volume injections typical with subcutaneous bolus injections. The active agent that is formed into the composition of the disclosure exhibits unaltered pharmacokinetic and pharmacodynamic properties when injected into mammals

BACKGROUND OF THE DISCLOSURE

Field of the Disclosure

Several techniques have been used in the past for the manufacture of biopolymer nano- and microparticles. Conventional techniques include spray drying and milling for particle formation and can be used to produce particles of 5 microns or less in size.

U.S. Pat. No. 5,654,010 and U.S. Pat. No. 5,667,808 describe the production of a solid form of recombinant human growth hormone, hGH, through complexation with zinc in order to create an amorphous complex, which is then micronized through an ultrasound nozzle and sprayed down in liquid nitrogen in order to freeze the droplets. The liquid nitrogen is then allowed to evaporate at a temperature of −80° C. and the resultant material is freeze-dried.

Microparticles and microspheres are solid or semi-solid particles having a diameter of less than one millimeter, typically less than 100 microns and may be less than 10 microns, which can be formed of a variety of materials, including proteins, synthetic polymers, polysaccharides and combinations thereof. Microspheres have been used in many different applications, primarily separations, diagnostics, and active agent delivery.

In the controlled active agent delivery area, molecules are often incorporated into or encapsulated within small spherical particles or incorporated into a monolithic matrix for subsequent release. A number of different techniques are routinely used to make these microspheres from synthetic polymers, natural polymers, proteins and polysaccharides, including phase separation, solvent evaporation, coacervation, emulsification, and spray drying. Generally the polymers form the supporting structure of these microspheres, and the active agent of interest is incorporated into the polymer structure.

Particles prepared using lipids to encapsulate target active agents are currently available. Liposomes are spherical particles composed of a single or multiple phospholipid and/or cholesterol bilayers. Liposomes are 100 nanometers or greater in size and may carry a variety of water-soluble or lipid-soluble active agents. For example, lipids arranged in bilayer membranes surrounding multiple aqueous compartments to form particles may be used to encapsulate water soluble active agents for subsequent delivery as described in U.S. Pat. No. 5,422,120 to Sinil Kim.

There is an on-going need for development of new methods for making particles, particularly those that can be adapted for use in the active agent delivery, separation and diagnostic areas. The most desirable particles from a utility standpoint would be small spherical particles that have the following characteristics: narrow size distribution, substantially spherical, substantially consisting of only the active agent, retention of the biochemical integrity and of the biological activity of the active agent. Further, the method of fabrication of the small spherical particles would have the following desirable characteristics: simple fabrication, an essentially aqueous process, high yield, and requiring no subsequent sieving. Also desirable is a particle formulation that retains the pharmacokinetic and pharmacodynamic properties of the active agent. The pharmacodynamic parameters of an active agent reflect its biochemical and physiological effects on the body. The pharmacokinetic (PK) parameters of an active agent reflect its particular metabolism in the body, and a measurement of PK parameters may be used to monitor active agent behavior.

There is a strong correlation between measured PK parameters and the pharmacodynamic properties of an active agent. For example, the correlation between an effective dose and PK parameters may be well established for a particular active agent, and PK parameters may be used to determine if it is necessary to modify dosing regimens or to determine if there is a change in patient physiology that is affecting active agent metabolism. In some cases, it may be difficult to directly quantitate the therapeutic effects of an active agent until the completion of a long course of treatment, and the measurement of PK parameters may be used as one measure of active agent behavior during treatment. For example, the PK properties of antibodies given to treat cancer or other diseases may be monitored during treatment. It would be advantageous to have a formulation that exhibits substantially the same value for established PK parameters compared to non-particle forms of the active agent but has the advantages of a formulation that takes the form of a particle. It would also be advantageous to have a particle formulation that does not cause an immunological stimulus that leads to an immune reaction. Such a reaction may occur, for example, if the particle does not dissolve readily and forms a depot at the site of injection. Measured pharmacokinetic parameters may include but are not limited to $C_{max}$ (peak serum concentration), $T_{max}$ (time to reach $C_{max}$), AUC (area under the serum concentration curve) and $F_{rel}$ (relative bioavailability). The measured PK parameters may be determined in a particular medium and are typically determined in vivo where the medium may be the bloodstream or some other part of the body. Inasmuch as PK determinations are made in a medium, PK values typically are determined for compositions containing a material or active agent of interest, such as a protein.

A protein is a sequence of amino acids for which the chain length is sufficient to produce the higher levels of tertiary and/or quaternary structure. This is to distinguish from 'peptides' or other small molecular weight active agents that do not have such structure.

An antibody (immunoglobulin) is a protein produced by immune system cells (B lymphocytes) in response to a foreign molecule (antigen) or invading organism. An antibody often binds to the foreign molecule or cell extremely tightly, thereby inactivating it or marking it for destruction by phagocytosis or complement-induced lysis. Higher vertebrates have five classes of immunoglobulins—IgA, IgD, IgE, IgG, and IgM—each with different role in the immune response.

A monoclonal antibody (mAb) is a highly specific, purified antibody (immunoglobulin molecule) that is derived from only one clone of immune system cells (B lymphocytes) and recognizes a specific site of only one foreign molecule (antigen). Monoclonal antibodies can be mass produced by laboratory manipulations (murine, chimeric, humanized). The term "monoclonal antibody" is used in a broader sense and specifically covers monoclonal antibodies which have an immunoglobulin Fc regions antibody compositions with polyepitopic specificity, bispecific antibodies, diabodies, and single-chain molecules, as well as antibody fragments (e.g., Fab, F(ab')$_2$, and Fv).

Monoclonal antibodies (mAbs) can be a laboratory-derived population of antibodies derived from one clone of cells and are highly specific in binding one particular antigen site. They are large proteins, in the order of 150 kDa, comprised of four polypeptide chains: two light chains of about 25 kDa each and two heavy chains of about 50 kDa each. Due to their large molecular weight, solutions of monoclonal antibodies may be very viscous and are currently delivered by intravenous injection.

Polyclonal antibodies are a range of antibodies (immunoglobulin molecules) that are specific for many sites of a single foreign molecule (antigen). Natural immune responses are polyclonal. Purified preparations of antibodies from serum are also used in various therapeutic applications. One such preparation, termed IVIG, represents purified IgG antibodies from blood. Such preparations are often used to confer passive immunity on immunosuppressed individuals.

Antibodies referred to as trap molecules are composed of fusions between two distinct receptor components and a portion of an antibody molecule called the "Fc region", resulting in the generation of growth factor and cytokine blockers with markedly increased affinity over that offered by single component reagents Trap molecules, for example, have been developed by Regeneron Pharmaceuticals.

Antibodies often need to be delivered at relatively large quantities in order to achieve therapeutic effect. For instance, the delivery dose for many antibodies is between about 100 to 800 mg. Injectability of these large quantities of material present substantial formulation and delivery challenges. A small volume of such large dosage will typically have high viscosity; therefore, large volumes, on the order of well in excess of 10 mls, such as about 500 mls, and at times between about 250 and 500 mils, are needed to deliver it intravenously. Intravenous delivery is very uncomfortable to the patient, requires clinical settings, and it is both expensive and time consuming.

Rapid dissolving microparticle technology according to the disclosure can offer significant advantages for this market, because it allows formation of highly concentrated suspensions that are less viscous than formulations where the agent is in a highly concentrated soluble form but the microparticles dissolve rapidly and the active agent exhibits unchanged pharmacokinetic and pharmacodynamnic parameters Furthermore, the particle formulations can be readily solubilized upon injection and retain the pharmacokinetic and pharmacodynamic properties of the agent when injected in soluble form. Similarly, other active agents comprising high molecular weight proteins can benefit from the present disclosure. The disclosure describes compositions that can be delivered at high concentrations and at relatively small volumes, thus compositions with syringability and injectability properties. Prior to the present disclosure, monoclonal antibodies, other antibodies, or other high molecular weight proteins with a molecular weight above about 25 kDa, could not be injected at high concentrations using a fine bore needle, such as a 20 gauge and finer, 21 gauge and finer, 22 gauge and finer, 23 gauge and finer, 24 gauge and finer, 25 gauge and finer, 26 gauge and finer, 27 gauge and finer or 28 gauge and finer, needle used in connection with a standard syringe. Nor could such a protein be delivered, prior to the disclosure, in a small volume such as 10 ml or less, 9 ml or less, 8 ml or less, 7 ml or less, 6 ml or less, 5 ml or less, 4 ml or less, 3 ml or less or in a volume consistent with subcutaneous delivery such as 2 ml or less or 1 ml or less containing a clinically effective dose of the protein. The use of microparticle technology in connection with these molecules solves the problem of high volume injection of these molecules as previously required. Moreover, the formulation of the active agent does not alter the pharmacodynamic and pharmacokinetic parameters. This disclosure also can be useful in assisting in delivering lower molecular weight protein materials at high concentrations within a small injection volume and during a short delivery time. According to the disclosure, a volume consistent with delivery by injection, such as 2 mls or less, may be delivered in a clinically acceptable time frame, such as 2 minutes or less, with a clinically acceptable amount of force.

The manufacturing process for a monoclonal antibody is a tedious process, which explains its high price. Thus, it is important that mAbs are precisely delivered to a target location in a very efficient and safe manner. Also important in the preparation and delivery of microparticles, whether mAbs or not, is high yield formation of readily soluble microparticles or microspheres, the retention of their respective chemical integrities, and in the case of materials such as mAbs, very good injectability that may allow delivery by the subcutaneous, ocular, or other administration routes.

An aspect or object of the disclosure is to provide a substantially amorphous or non-crystalline antibody microparticle.

Another aspect or object of the present disclosure is to provide a syringable composition including substantially amorphous or non-crystalline antibody microparticles.

A further aspect or object of this disclosure is to provide a syringable composition providing a clinically effective dose of protein in about 10 ml or less of the composition, even when the protein has a molecular weight of about 25,000 Daltons and above.

A further aspect or object of this disclosure is to provide a syringable composition providing a clinically effective dose of protein in about 2 mL or less of the composition, even when the protein has a molecular weight of about 25,000 Daltons and above.

A further aspect or object of the present disclosure is to provide microparticles having at least about 50 mg of active agent per ml of a clinically effective dose, finding especially advantageous application when the active agent has a molecular weight of at least about 25,000 Daltons.

Another aspect or object of the disclosure is to provide a method of using microparticles in clinically effective manners through active agent delivery by injection at high concentrations such as but not limited to subcutaneous injection.

A further aspect or object of the present disclosure is a process for preparing microparticles of protein materials of relatively high molecular weight.

Another object or aspect of the present disclosure is to provide microparticles, typically microspheres, which are readily soluble, i.e. exhibit solubility within about ten minutes in a PBS buffer at physiological pH, while exhibiting chemical integrity, i.e. at least about 90 percent of the compound is chemically intact in the microparticles, and which exhibit injectability, more particularly in the form of syringability, i.e. form at least a 50 mg/ml suspension and deliverability of the suspension through a fine bore needle without use of excessive force.

Another aspect or object of the present disclosure is to provide microparticles of an active agent that retain the established pharmacokinetic and pharmacodynamic properties of the active agent.

Other aspects, objects and advantages of the present disclosure will be understood from the following description according to the embodiments of the present disclosure, specifically including stated and unstated combinations of the various features which are described herein, relevant information concerning which is shown in the accompanying drawings.

SUMMARY OF THE DISCLOSURE

The present disclosure relates to protein microparticles having injectable properties at high doses. The protein is an active agent, and the microparticles are substantially amorphous or non-crystalline. With these compositions, very high concentrations of active agent are deliverable in very small volumes. The active agent in these microparticles displays unaltered pharmacodynamic and pharmacokinetic properties compared to those properties when administered in soluble form.

The active agent of the present disclosure can be a therapeutic agent or a diagnostic agent. In a typical embodiment of the present disclosure, the active agent is a macromolecule such as a protein, including an antibody including monoclonal antibodies. In another embodiment, the particles containing the active agent are suitable for in vivo delivery to a subject in need of the agent by any suitable route, including subcutaneous and/or ocular injection approaches, which are otherwise not feasible for macromolecules of these types.

The present disclosure also relates to methods of production and methods of use of microparticles that retain pharmacokinetic and pharmacodynamic properties, including small spherical particles or microspheres of an active agent. In accordance with a method of production, the active agent is dissolved in a solvent containing a dissolved phase-separation enhancing agent to form a solution that is a single liquid phase. The solvent may be an aqueous or aqueous-miscible solvent. The solution is then subjected to a liquid-solid phase separation having the active agent comprising the solid phase and the PSEA and solvent comprising the liquid phase. The liquid-solid phase separation can be induced in numerous ways, such as changing the temperature of the solution to below the phase transition temperature of the solution.

In an embodiment of the present disclosure, the method of subjecting the solution to a liquid-solid phase separation is by cooling the solution to below the phase transition temperature of the active agent in the solution. That temperature may be above or below the freezing point of the solution. For solutions in which the freezing point is above the phase transition temperature, the solution can include a freezing point depressing agent, such as polyethylene glycol or propylene glycol, to lower the freezing point of the solution to allow the phase separation in the solution to occur without freezing the solution.

The phase-separation enhancing agent of the present disclosure enhances or induces the liquid-solid phase separation of the active agent in the solution when the solution is subjected to the step of phase change in which the active agent solidifies to form a suspension of small spherical particles as a discontinuous phase while the phase-separation enhancing agent remains dissolved in the continuous phase. That is, the phase separation enhancing agent does not go through a change of phase, but the active agent does go through a phase change.

The method of producing the particles in the present disclosure may also include an additional step of controlling the liquid-solid phase separation of the particles to control the size and shape of the particles formed. Methods of controlling the phase-separation include control of the ionic strength, the pH, the concentration of the phase-separation enhancing agent, the concentration of the active agent in the solution, or controlling the rate of change in temperature of the solution, the control of these being either before the phase-separation or a change of any or several of these in order to induce the phase-separation.

In another embodiment of the present disclosure, the small spherical particles are separated from the PSEA in the continuous phase after particle formation. In a further embodiment, the method of separation is by washing the solution containing the particles with a liquid medium in which the active agent is not soluble in the liquid medium while the phase-separation enhancing agent is soluble in the liquid medium. The liquid washing medium may contain an agent which reduces the solubility of the active agent in the liquid medium. The liquid washing medium may also contain one or more excipients. The excipient may act as a stabilizer for the small spherical particles or for the active agent or the carrier agent. The excipient may also imbue the active agent or the particle with additional characteristics such as controlled release of the active agent from the particles or modified permeation of the active agent through biological tissues.

In another embodiment, while the small particles do not include the PSEA, they may be harvested in the presence of the PSEA phase for subsequent processing steps prior to separation from the PSEA phase. In another embodiment, the solution is an aqueous solution comprising an aqueous or aqueous-miscible solvent.

BRIEF DESCRIPTION OF THE DRAWINGS

FIG. 22b is the same plot as FIG. 22a but on a different scale.

DESCRIPTION OF THE ILLUSTRATED EMBODIMENTS

Figure 1:
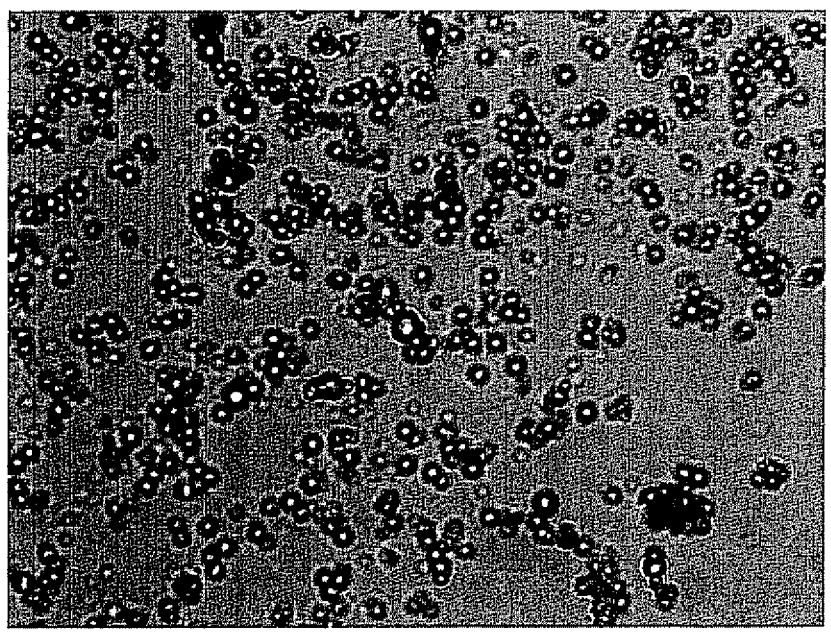
FIG. 1 gives optical microscope images of anti-Factor VIII monoclonal antibody microspheres prepared as described in Example 3.
Figure 1:
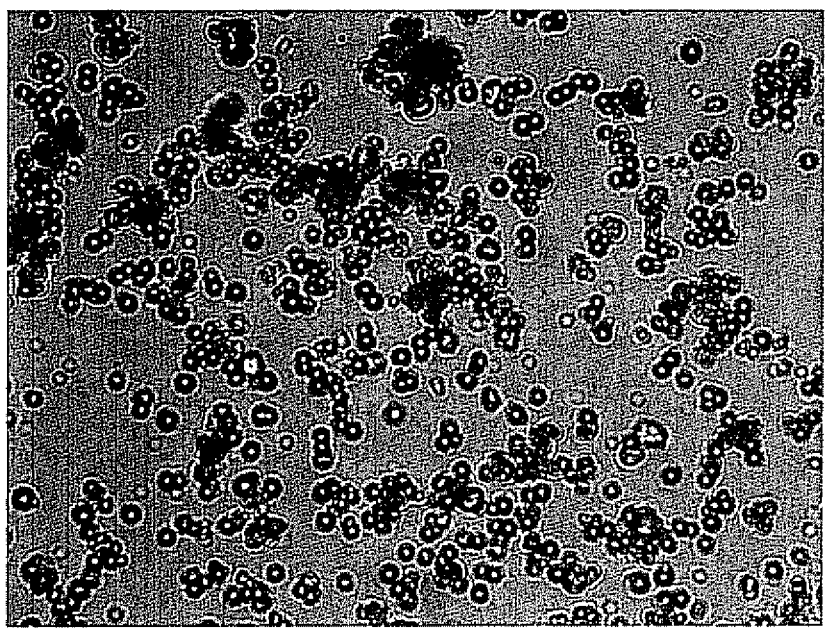

The present disclosure is susceptible to embodiments in many different forms. The embodiments are disclosed with the understanding that the present disclosure is to be considered as exemplifications of the principles of the disclosure and are not intended to limit the broad aspects of the disclosure to the embodiments illustrated.

As required, detailed embodiments of the present disclosure are disclosed herein; however, it is to be understood that the disclosed embodiments are merely exemplary of the disclosure, which may be embodied in various forms. Therefore, specific details herein are not to be interpreted as limiting, but merely as a basis for the claims and as a representative basis for teaching one skilled in the art to variously employ the present disclosure in virtually any appropriate manner.

The present disclosure is related to compositions of substantially amorphous or non-crystalline small particles of an active agent that is a protein. Special application is found when the active agent has a molecular weight of at least about 25,000 Daltons. The present disclosure relates to compositions of small particles, which can be substantially spherical in shape, of an active agent. Active agents that can benefit from the present approach are high molecular weight proteins, especially substantially amorphous forms of high molecular weight proteins, including substantially amorphous monoclonal antibodies. The disclosure has the capability of providing injectable or syringeable compositions of thigh molecular weight proteins, including monoclonal antibodies, at high concentrations, and accordingly provides the ability to deliver a clinically effective dose of such active agents with a low volume of composition, that may be 10 ml or less of composition, and typically with a volume found in a standard syringe. According to the disclosure, active agents of the present particles exhibit the same pharmacodynamic and pharmacokinetic properties as the active agent when administered in a soluble form. Although not wishing to be bound by any particular theory, it is believed that the particles of the disclosure dissolve rapidly in vivo when administered and are not taken up by the cells of the immune system, thereby resulting in values for pharmacodynamic and pharmacokinetic properties similar to the active agent delivered in soluble form. It is believed that solubility of an active agent in vitro may be used to determine if that active agent will exhibit established PK parameters in vivo when in particle form. Such an active agent may display an in vitro solubility of 0.5 mg/ml or greater, or 1 mg/ml or greater, under in vitro conditions that are similar to in vivo conditions.

In accordance with the method of production, the active agent is dissolved in a solvent containing a dissolved phase-separation enhancing agent to form a solution that is a single liquid continuous phase. The solvent may be an aqueous or aqueous-miscible solvent. The solution is then subjected to a phase change, for example, by lowering the temperature of the solution to below the phase transition temperature of the active agent, whereby the active agent goes through a liquid-solid phase separation to form a suspension of substantially amorphous or non-crystalline small particles constituting a discontinuous phase while the phase-separation enhancing agent remains in the continuous phase.

The present invention relates to compositions of small particles, typically substantially spherical in shape, of an active agent. The active agents may be high molecular weight proteins, including substantially amorphous forms of high molecular weight proteins, such as substantially amorphous monoclonal antibodies. The invention has the capability of providing injectable or syringable compositions of high molecular weight proteins, including monoclonal antibodies, at high concentrations, and accordingly provides the ability to deliver a clinically effective dose of such active agents with a low volume of composition, typically with 10 nm or less, or even 2 ml or less, of composition, and more typically with a volume typically found in a standard syringe. Moreover, the composition may be delivered by injection in a clinically acceptable time frame, such as 2 minutes or less, with a clinically acceptable amount of force. A clinically effective amount of force can be considered be that amount of force that could be produced by an individual such as medical personnel or the patient.

Methods of production and methods of use of these compositions of small spherical particles of an active agent are also contemplated by this disclosure. In accordance with the method of production, the active agent is dissolved in an aqueous or aqueous-miscible solvent containing a dissolved phase-separation enhancing agent (PSEA) to form a solution in a single liquid phase. The solution then is subjected to a liquid-solid phase separation having the active agent comprising the solid phase and the PSEA and solvent comprising the liquid phase. The liquid-solid phase separation can be induced in numerous ways, such as changing the temperature of the solution, for example by lowering the temperature of the solution to below the phase transition temperature of the active agent and/or by energy addition. The method is most suitable for forming small spherical particles of therapeutic agents which can be delivered to a subject in need of the therapeutic agent. The method is also most suitable for forming solid, small spherical particles of macromolecules, particularly macromolecules which are heat labile, such as proteins, including monoclonal antibody materials. The disclosure has the capability of providing syringable macromolecules.

The Active Agent

The active agent of the present disclosure is a protein which can be a therapeutic agent or a diagnostic agent. Advantageously, the active agents are high molecular weight proteins Typical agents are amorphous forms of proteins, including amorphous antibodies.

When used herein, the term antibody encompasses monoclonal antibodies, polyclonal antibodies, preparations of antibody fractions from serum and antibody fragments, especially the antigen-binding fractions generally known as "Fab" fragments or regions, single chain antibodies, as well as monoclonal or polyclonal antibodies or other antibodies in recombinant form, and are what are currently recognized in the art by the designation "trap molecule" Antibodies also refers to any of the aforementioned forms of antibodies that are treated, such as by coating or encapsulating, including by approaches as described herein.

Trap molecules are composed of fusions between two distinct receptor components and a portion of an antibody molecule referred to as the "Fc region" resulting in the generation of growth factor and cytokine blockers with markedly increased affinity over that offered by single-component reagents.

The following references provide further information on trap molecules: "Cytokine Traps: Multi-Component, High-Affinity Blockers of Cytokine Action"; Economides A N, Carpenter L R, Rudge J S, Wong V, Koehler-Stec E M, Hartnett C, Pyles E A, Xu X, Daly T J, Young M R, Fandl J P, Lee F, Carver S, McNay J, Bailey K, Ramakanth S, Hutabarat R, Huang T T, Radziejewski C, Yancopoulos G D, Stahl N; Journal: Nat Med (2003); Volume, (Number), Pages: 9(1):47-52. "Vascular Endothelial Growth Factor-Trap Decreases Tumor Burden, Inhibits Ascites, and Causes Dramatic Vascular Remodeling in an Ovarian Cancer Model"; Byrne A T, Ross L, Holash J, Nakanishi M, Hu L, Hofmann J I, Yancopoulos G D, Jaffe R B; Journal: Clin Cancer Res (2003); Volume, (Number), Pages: 15; 9(15):5721-8. "Prevention of Thecal Angiogenesis, Antral Follicular Growth, and Ovulation in the Primate by Treatment with Vascular Endothelial Growth Factor Trap R1R2"; Wulff C, Wilson H, Wiegand S J, Rudge J S, Fraser A M; Journal: Endocrinology (2002); Volume, (Number), Pages: 143(7):2797-807. Volume, (Number), Pages: 143(7):2797-807.

In an exemplary embodiment of the present disclosure, the active agent is a monoclonal antibody, which can be natural or synthetic. Examples of monoclonal antibodies include, but are not limited to: adalimutab (available from Abbott under the tradename HUMIRA®), abciximab (for addressing cardiovascular disease; available from Centocor under the tradename REOPRO®); daclizumab (immunosuppressant for transplantation, available from Roche under the tradename ZENAPAZT™), rituximab (non-Hodgkin's lymphoma treatment; available from IDEC/Genentech under the tradename RITUXIN® or RITUXAN®), basiliximab (immunosuppressant; available from Novartis under the tradename SIMULECT®), palivzumab (for prevention of respirator synctial virus; available from Medimmune under the tradename SYNAGIS®), infliximab (inflammatory diseases treatment; available from Centocor under the tradename REMICADE®), trastuxumab (breast cancer treatment; available from Genentech under the tradename HERCEPTIN®), gemtuzumab (bone marrow cancer treatment; available from IDEC under the tradename MYLOTARG®), alemzutumab (leukemia treatment; available from Millennium/ILEX under the tradename CAMPATH®), and ibritumomab (lymphoma treatment; available from IDEC under the tradename ZEVULIN™).

In another embodiment of the disclosure, the active agent is a preparation of antibodies prepared from serum. One such preparation is Gammagard Liquid (available from Baxter Healthcare Corporation, Westlake Village, Calif.) which is a ready-for-use sterile, liquid preparation of highly purified and concentrated immunoglobulin G (IgG) antibodies often used to treat immunosuppressed individuals.

Examples of antibody "Fab" fractions or regions include, but are not limited to, the following. TGX-6B4, currently in development by ThromboGenics Ltd of Dublin, Ireland, is an antibody to GP1b which inhibits platelet adhesion and is indicated to be a novel approach to prevent early steps in arterial thrombosis. Digoxin specific Fab fragments have been reported to be beneficial in the treatment of toad venom poisoning. (Heart 200.3; 89: 12-472, Toxalert, 15: issue 1, 1998). Humanized Fab fragments have been shown to recognize the IgE-binding domain of human Fc(epsilon)RIalpha in COS and CHO cells. (Journal of Biochemistry, 2001: Vol 129, Issue 15-12). Other information concerning Anti-tumor Radioimmnunotherapy using multivalent Fab' fragments is found in British Journal of Cancer (1999) 81, 972-980.

Examples of other high molecular weight proteins include but are not limited to AAT, DNase, superoxide dismutase, subtilisin and other proteins. Typically, high molecular weight indicates a protein having molecular weights on the order of approximately 25,000, depending on particular needs or properties of the protein or to its intended use. Lower molecular weight proteins can benefit from the disclosure to the extent same needs to be administered, for example by injection, in high concentrations. Such proteins are known in the art; see for example U.S. patent application Ser. No. 10/894,410 filed Jul. 19, 2004 and No. 10/896,326 filed Jul. 21, 2004.

The Microparticles, Small Spherical Particles or Microspheres

The microparticles or the microspheres of the present disclosure usually have an average geometric particle size of less than 200 microns, typically from about 0.01 µm to about 200 µm, typically not more than about 50 µm, and can be from 0.1 µm to 10 µm, or from about 0.5 µm to about 5 µm, and may be from about 0.5 pin to about 3 μm, as measured by dynamic light scattering methods (e.g., photocorrelation spectroscopy, laser diffraction, low-angle laser light scattering (LALLS), medium-angle laser light scattering (MALLS)), by light obscuration methods (Coulter analysis method, for example) or by other methods, such as rheology or microscopy (light or electron).

The small spherical particles or microspheres are substantially spherical. What is meant by "substantially spherical" is that the ratio of the lengths of the longest to the shortest perpendicular axes of the particle cross section is less than or equal to about 1.5. Substantially spherical does not require a line of symmetry. Further, the particles may have surface texturing, such as lines or indentations or protuberances that are small in scale when compared to the overall size of the particle and still be substantially spherical. Typically, the ratio of lengths between the longest and shortest axes of the particle is less than or equal to about 1.33. The ratio of lengths between the longest and shortest axes of the particle may be less than or equal to about 1.25. Surface contact is minimized in microspheres that are substantially spherical, which minimizes the undesirable agglomeration of the particles upon storage. Many crystals or flakes have flat surfaces that can allow large surface contact areas where agglomeration can occur by ionic or non-ionic interactions. A sphere permits contact over a much smaller area.

The microparticles also can have substantially the same particle size, Particles having a broad size distribution where there are both relatively big and small particles allow for the smaller particles to fill in the gaps between the larger particles, thereby creating new contact surfaces. A broad size distribution can result in larger spheres by creating many contact opportunities for binding agglomeration. The spherical microparticles of the disclosure typically are within a narrow size distribution, thereby minimizing opportunities for contact agglomeration. What is meant by a "narrow size distribution" is a particle size distribution that has a ratio of the volume diameter of the $90^{th}$ percentile of the small spherical particles to the volume diameter of the $10^{th}$ percentile less than or equal to 5. The volume diameter of the $90^{th}$ percentile of the small spherical particles to the volume diameter of the $10^{th}$ percentile can be less than or equal to 3. Typically, the ratio of the volume diameter of the $90^{th}$ percentile of the small spherical particles to the volume diameter of the $10^{th}$ percentile is less than or equal to 2.

Geometric Standard Deviation (GSD) can also be used to indicate the narrow size distribution. GSD calculations involved determining the effective cutoff diameter (ECD) at the cumulative less than percentages of 15.9% and 84.1% GSD is equal to the square root of the ratio of the ECD less than 84.17% to ECD less then 15.9%. The GSD has a narrow size distribution when GSD<2.5, and may be less than 1.8.

In a typical form of the disclosure, the active agent in the microparticle or microsphere is semi-crystalline or non-crystalline or substantially amorphous.

The microspheres can be comprised of active agents which are substantially amorphous or non-crystalline, that is they are in an amorphous or semi-crystalline form. As used herein, "amorphous" refers to a generally random solid form of the active agent wherein crystalline lattices of the protein(s) or other active agent(s) within the microsphere are absent, and "semi-crystalline" refers to a generally random solid form of active agent(s) wherein the active agent content of the microsphere is comprised of less than 50% of crystalline lattice forms of the active agent(s).

Typically, the microparticles or microspheres are substantially nonporous and have a density greater than 0.5 g/cm³, greater than 0.75 g/cm³ or greater than about 0.85 g/cm³. A typical range for the density is from about 0.5 g/cm³ to about 2 g/cm³ and can be from about 0.75 g/cm³ to about 1.75 g/cm³ or from about 0.85 g/cm³ to about 1.5 g/cm³. The substantially amorphous or non-crystalline microparticles according to the disclosure are more readily soluble or exhibit a rate of dissolution faster than microparticles which are not so constituted, such as crystalline microparticles.

The microparticles or microspheres of the present disclosure can exhibit a high content of the active agent. There is no requirement for a significant quantity of bulking agents or similar excipients that are required by many other methods of preparing microparticles, although materials in addition to the active agent can be included as desired to achieve a particular objective or objectives. For example, in many applications, the microspheres comprise equal to or greater than 95% by weight of the particles. Typically, the active agent is present from about 20% to 100% by weight of the particle, may be from about 50% to about 100% by weight, from about 80% to about 100% by weight, and even from about 90% to about 100% by weight. When stating ranges herein, it is meant to include any range or combination of ranges therein.

A further aspect of the present disclosure is that the microparticles or microspheres retain the biochemical integrity and the biological activity of the active agent with or without the inclusion of excipients. According to the disclosure, the active agent in microparticles exhibits similar pharmacokinetic and pharmacodynamic properties relative to formulations and compositions that use the active agent in a soluble form.

In Vivo Delivery of the Particles

Microparticles, small spherical particles or microspheres containing the active agent in the present disclosure are suitable for in vivo delivery to a subject in need of the agent by an injectable route. An especially suitable delivery route is injectable, which includes intravenous, intramuscular, subcutaneous, intraperitoneal, intrathecal, epidural, intra-arterial, intra-articular and the like. Other delivery routes, such as topical, oral, rectal, nasal, pulmonary, vaginal, buccal, sublingual, transdermal, transmucosal, otic or intraocular, could be practiced, but typically the advantages of the disclosure are more evident for injection applications. Often most advantageous for the purposes of this disclosure is the syringable delivery route. Importantly, the microparticles or microspheres can be aspirated into a syringe and injected through fine needles despite the high molecular weight of the proteins or active agents. A suitable delivery route is injection with a fine needle, which includes subcutaneous, ocular and the like. By fine bore needle is meant needles of at least 20 Gauge size, typically between about 22 Gauge and about 30 Gauge and above. Advantageously, the fine bore needles can be at least as fine as 24 Gauge, more advantageously at least as fine bore as 26 gauge, and even more advantageously at least as fine as 28 Gauge.

The microparticles or microspheres are capable of being injected at a concentration of at least about 50 mg of protein per ml of the composition being injected. For example, from about 100 to about 800 mg of protein are injectable in a delivery volume if not more than about 10 ml, and usually at least about 2 ml for many applications. Also, the delivery is made during a normal injection time periods. Typically such time periods are not more than about 20 seconds or less.

The present method for particle formation set forth herein provides for particle formation with or without excipients or other components or additives as desired or required. Fabrication of protein microparticles or microspheres from protein itself with no additives is also an approach according to the disclosure and at time provides superior advantages for use. A volume consistent with delivery by injection, such as 2 mls or less, may be delivered in a clinically acceptable time frame, such as 2 minutes or less, with a clinically acceptable amount of force.

Methods for Making Microparticles

The Continuous Phase

The method of the present disclosure of preparing microparticles or microspheres of an active agent begins with providing a solution having the active agent and a phase-separation enhancing agent dissolved in a first solvent in a single liquid phase. The solution can be an organic system comprising an organic solvent or a mixture of miscible organic solvents. The solution can also be an aqueous-based solution comprising an aqueous medium or an aqueous-miscible organic solvent or a mixture of aqueous-miscible organic solvents or combinations thereof. The aqueous medium can be water, normal saline, buffered solutions, buffered saline, and the like. Suitable aqueous-miscible organic solvents include, but are not limited to, N-methyl-2-pyrrolidinone (N-methyl-2-pyrrolidone), 2-pyrrolidinone (2-pyrrolidone), 1,3-dimethyl-2-imidazolidinone (DMI), dimethylsulfoxide, dimethylacetamide, acetic acid, lactic acid, acetone, methyl ethyl ketone, acetonitrile, methanol, ethanol, isopropanol, 3-pentanol, n-propanol, benzyl alcohol, glycerol, tetrahydrofuran (THE), polyethylene glycol (PEG), PEG-4, PEG-8, PEG-9, PEG-12, PEG-14, PEG-16, PEG-120, PEG-75, PEG-150, polyethylene glycol esters, PEG-4 dilaurate, PEG-20 dilaurate, PEG-6 isostearate, PEG-8 palmitostearate, PEG-150 palmitostearate, polyethylene glycol sorbitans, PEG-20 sorbitan isostearate, polyethylene glycol monoalkyl ethers, PEG-3 dimethyl ether, PEG-4 dimethyl ether, polypropylene glycol (PPG), polypropylene alginate, PPG-10 butanediol, PPG-10 methyl glucose ether, PPG-20 methyl glucose ether, PPG-15 stearyl ether, propylene glycol dicaprylate/dicaprate, propylene glycol laurate, and glycofurol (tetrahydrofurfuryl alcohol polyethylene glycol ether), alkanes including propane, butane, pentane, hexane, heptane, octane, nonane, decane, or a combination thereof.

The single continuous phase can be prepared by first providing a solution of the phase-separation enhancing agent, which is either soluble in or miscible with the first solvent. This is followed by adding the active agent to the solution. The active agent may be added directly to the solution, or the active agent may first be dissolved in a second solvent and then together added to the solution. The second solvent can be the same solvent as the first solvent, or it can be another solvent selected from the list above and which is miscible with the solution. In typical situations, the active agent is added to the solution at an ambient temperature or lower, which is important particularly for heat labile molecules, such as certain proteins. What is meant by "ambient temperature" is a temperature of around room temperature of about 20° C. to about 40° C. However, the system can also be heated to increase the solubility of the active agent in the system as long as heating does not cause significant reduction in the activity of the agent.

The Phase-Separation Enhancing Agent

The phase-separation enhancing agent (PSEA) of the present disclosure enhances or induces the liquid-solid phase separation of the active agent from the solution when the solution is subjected to the step of phase separation in which the active agent becomes solid or semi-solid to form a suspension of small spherical particles as a discontinuous phase while the phase-separation enhancing agent remains dissolved in the continuous phase. The phase-separation enhancing agent reduces the solubility of the active agent when the solution is brought to the phase separation conditions. Suitable phase-separation enhancing agents include, but are not limited to, polymers or mixtures of polymers that are soluble or miscible with the solution. Examples of suitable polymers include linear of branched polymers, copolymers and block copolymers. These polymers can be water soluble, semi-water soluble, water-miscible, or insoluble.

In an exemplary form of the disclosure, the phase-separation enhancing agent is water soluble or water miscible. Types of polymers that may be used include carbohydrate-based polymers, polyaliphatic alcohols, poly(vinyl) polymers, polyacrylic acids, polyorganic acids, polyamino acids, copolymers and block co-polymers (e.g., poloxamers such as Pluronic F127 or F68), tert-polymers, polyethers, naturally occurring polymers, polyimides, surfactants, polyesters, branched and cyclo-polymers, and polyaldehydes.

Especially suitable polymers are ones that are acceptable as pharmaceutical additives for the intended route of administration of the active agent particles, Included polymers are pharmaceutically acceptable additives such as polyethylene glycol (PEG) of various molecular weights, such as PEG 200, PEG 300, PEG 3350, PEG 8000, PEG 10000, PEG 20000, etc. and poloxamers of various molecular weights such as poloxamer 188 and Pluronic F127 or Pluronic F68. Other polymers are polyvinylpyrrolidone (PVP) and hydroxyethylstarch. Other amphiphilic polymers can also be used alone or in combinations. The phase-separation enhancing agent can also be a non-polymer such as a mixture of propylene glycol and ethanol.

Liquid-Solid Phase Separation

A liquid-solid phase separation of the active agent in the solution can be induced by any method known in the art, such as change in temperature (either raising or lowering), change in pressure, change in pH, change in ionic strength of the solution, change in the concentration of the active agent, change in the concentration of the phase-separation enhancing agent, change in osmolality of the solution, combinations of these, and the like.

In a one embodiment of the present disclosure, the phase change is a temperature-induced phase change. In many embodiments, the temperature-induced phase change is effected by lowering the temperature below the phase transition temperature of the active agent in the solution.

Figure 13:
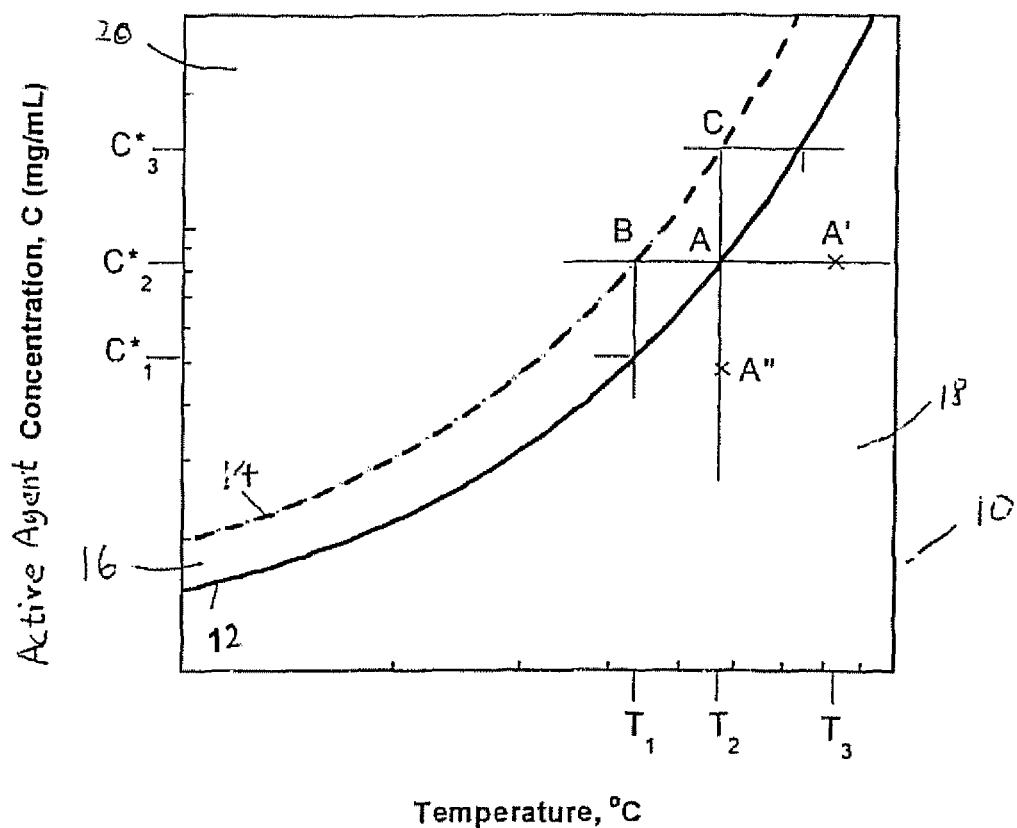
FIG. 13 is a two-dimensional phase diagram plotting active agent concentration against temperature.

FIG. 13 is a two-dimensional phase diagram 10 for the solution containing solvent, a PSEA and an active agent. The diagram plots the active agent concentration against the temperature of the solution. The concentration of the PSEA is held constant.

The diagram of FIG. 13 has a saturation curve 12; a supersaturation curve 14; a metastable area 16 there between; a first area 18 below the saturation curve where the system is in a homogenous, single liquid phase where all components are in the liquid phase; and a second area 20 above the supersaturation curve where the system is a two-phase system having a solid phase of the active agent and a liquid phase of the PSEA and solvent. The phase diagram is helpful in determining the temperature of the system and the relative concentration of components in the pure liquid phase, the liquid-solid phase and the conditions surrounding the transition between these two phases.

As disclosed herein, preparation of microparticles or microspheres of the active agent can involve cooling from an undersaturated solution (point A' in FIG. 13) reaching saturation at point A where the solution is in equilibrium with any solid phase that may be present. On further cooling, a state is reached where the solution contains more active agent than that corresponding to the equilibrium solubility at the given temperature; the solution thus becomes supersaturated. Spontaneous formation of the solid phase does not occur until point B is reached. Point B is a point on the boundary of the metastable zone. The metastable zone width can be expressed either by the maximum attainable undercooling $\Delta T_{max}=T_2-T_1$ or by the supersaturation $\Delta C_{max}=C^*_2-C^*_1$ These two expressions are thermodynamically equivalent:

$$\Delta C_{max} = C^*_2 - C^*_1 = \int_{T_1}^{T_2}\left(\frac{\partial C^*}{\partial T}\right)dT \cong \Delta T_{max}\left(\frac{dC^*}{dT}\right)$$

The path A'-A-B represents a polythermal method of preparing a metastable solution. In an isothermal process the starting point would be A''. By increasing the concentration at constant temperature, saturation will again be achieved at point A. An isothermal increase in concentration (by solvent evaporation or by seeding/addition of the active agent, for instance) to point C will cause the solution to move into the metastable region until the metastability limit is again reached. When the metastable limit is exceeded, the solution becomes unstable and a spontaneous formation of the solid phase immediately occurs.

The value $(\Delta C_{max})_1=C^*_3-C^*_2$ obtained isothermally can be different from the corresponding value of $\Delta T_{max}=T_3-T_2$ obtained polythermally. As the boundary of the metastable zone is approached, the time necessary for the solid particle formation decreases until the metastable limit is reached.

In the polythermal process, the rate of cooling is done at a controlled rate to control the size and shape of the particles. What is meant by a controlled rate is about 0.2° C./minute to about 50° C./minute, and may be from 0.2° C./minute to 30° C./minute. The rate of change can be at a constant or linear rate, a non-linear rate, intermittent, or a programmed rate (having multiple phase cycles). The particles can be separated from the PSEA in the solution and purified by washing as will be discussed below.

The present disclosure contemplates adjusting the concentration of the active agent, the concentration of the PSEA, the temperature or any combination of these to cause a phase change where the active agent goes from a liquid state to a solid state while the PSEA and solvent do not go through a phase change and remain as liquids. It is also contemplated changing the pH, the ionic strength, the osmolality and the like to enhance, promote, control or suppress the phase change. For solutions in which the freezing point is relatively high, or the freezing point is above the phase transition temperature, the solutions can include a freezing point depressing agent, such as propylene glycol, sucrose, ethylene glycol, alcohols (ergo, ethanol, methanol) or aqueous mixtures of freezing-point depression agents to lower the freezing point of the system to allow the phase change in the system without freezing the system. The process can also be carried out such that the temperature is reduced below the freezing point of the system. The process described herein is particularly suitable for molecules that are heat labile (e.g., proteins).

Optional Excipients

The microparticles of the present disclosure may include one or more excipients. The excipient may imbue the active agent or the microparticles with additional characteristics such as increased stability of the microparticles or of the active agents or of the carrier agents, controlled release of the active agent from the microparticles, or modified permeation of the active agent through biological tissues. Suitable excipients include, but are not limited to, carbohydrates (e.g., trehalose, sucrose, mannitol), cations (e.g., $Zn^{2+}$, $Mg^{2+}$, $Ca^{2+}$), anions (e.g. $SO_4^{2-}$), amino acids (e.g., glycine), lipids, phospholipids, fatty acids, surfactants, triglycerides, bile acids or their salts (e.g., cholate or its salts, such as sodium cholate; deoxycholic acid or its salts), fatty acid esters, and polymers present at levels below their functioning as PSEAs. When an excipient is used, the excipient does not significantly affect the phase diagram of the solution.

Separating and Washing the Particles

In an exemplary embodiment of the present disclosure, the microparticles or microspheres are harvested by separating them from the phase-separation enhancing agent in the solution. In a yet another embodiment, the method of separation is by washing the solution containing the microparticles or microspheres with a liquid medium in which the active agent is not soluble in the liquid medium while the phase-separation enhancing agent is soluble in the liquid medium. Some methods of washing may be by diafiltration or by centrifugation. The liquid medium can be an aqueous medium or an organic solvent. For active agents with low aqueous solubility, the liquid medium can be an aqueous medium or an aqueous medium containing agents that reduce the aqueous solubility of the active agent, such as divalent cations. For active agents with high aqueous solubility, such as many proteins, an organic solvent or an aqueous solvent containing a protein-precipitating agent such as ammonium sulfate may be used.

In an exemplary embodiment of the present disclosure, the microparticles or microspheres are harvested by separating them from the phase-separation enhancing agent in the solution. In yet another embodiment, the method of separation is by washing the solution containing the microparticles or microspheres with a liquid medium in which the active agent is not soluble in the liquid medium while the phase-separation enhancing agent is soluble in the liquid medium. Some methods of washing may be by diafiltration or by centrifugation. The liquid medium can be an aqueous medium or an organic solvent. For active agents with low aqueous solubility, the liquid medium can be an aqueous medium or an aqueous medium containing agent that reduces the aqueous solubility of the active agent, such as divalent cations. For active agents with high aqueous solubility, such as many proteins, an organic solvent or an aqueous solvent containing a protein-precipitating agent such as ammonium sulfate may be used.

Examples of suitable organic solvents for use as the liquid medium include those organic solvents specified above as suitable for the continuous phase, including methylene chloride, chloroform, acetonitrile, ethylacetate, methanol, ethanol, pentane, and the like. It is also contemplated to use mixtures of any of these solvents. One blend is methylene chloride or a 1:1 mixture of methylene chloride and acetone. The liquid medium may have a low boiling point for easy removal by, for example, lyophilization, evaporation, or drying.

The liquid medium also can be a supercritical fluid, such as liquid carbon dioxide or a fluid near its supercritical point. Supercritical fluids can be suitable solvents for the phase-separation enhancing agents, particularly some polymers, but are nonsolvents for protein particles. Supercritical fluids can be used by themselves or with a cosolvent. The following supercritical fluids can be used: liquid $CO_2$, ethane, or xenon. Potential cosolvents can be acetontitrile, dichloromethane, ethanol, methanol, water; or 2-propanol.

The liquid medium used to separate the microparticles or microspheres from the PSEA described herein, may contain an agent which reduces the solubility of the active agent in the liquid medium. It is most desirable that the particles exhibit minimal solubility in the liquid medium to maximize the yield of the microparticles or microspheres. For some proteins, such as insulin and the decrease in solubility can be achieved by the adding of divalent cations, such as $Zn^{2+}$ to the protein. Other ions that can be used to form complexes include, but are not limited to, $Ca^{2+}$, $Cu^{2+}$, $Fe^{2+}$, $Fe^{3+}$, and the like. The solubility of the complexes are sufficiently low to allow diafiltration of the complex in an aqueous solution.

The liquid medium may also contain one or more excipients which may imbue the active agent or the microparticles with additional characteristics such as increased stability of the mircroparticles and/or of the active or carrier agents, controlled release of the active agent from the particles, or modified permeation of the active agent through biological tissues as discussed previously. In another form of the disclosure, the microparticles or microspheres are not separated from the PSEA containing solution.

Aqueous-Based Process

In another embodiment, the fabrication process of the present system is of an aqueous system including an aqueous or an aqueous-miscible solvent. Examples of suitable aqueous-miscible solvents include, but are not limited to, those identified above for the continuous phase. One advantage of using an aqueous-based process is that the solution can be buffered and can contain excipients that provide biochemical stabilization to protect the active agents. This can be especially advantageous when the active agent is a proteins

EXAMPLE 1

This Example provides one procedure for preparation of 500 µl batches of syringeable anti-Factor VIII monoclonal antibody microspheres. Ten batches of 500 µl of the monoclonal antibody are prepared in Eppendorf tubes as follows:

Preparation of 40 mM Ammonium Acetate (AA) Buffer at pH6.5: 40 mM of AA buffer is prepared by dissolving 3.08 grams of AA (Spectrum) in 1 liter of deionized $H_2O$. The AA is readily soluble and forms a buffer solution with a pH of ~6.4, which is adjusted to pH6.5 with dilute ammonium hydroxide.

Preparation of 500 mL of 10% Poloxamer 188 in 40 mM AA Buffet solution: 50 grains of Poloxamer 188 (BASE) are dissolved in 500 mL of 40 mM AA Buffer, as described in step 1, but pH adjustment is not necessary). The dissolution of this quantity of Poloxamer can be accomplished in several additions. The final pH is around pH ~6.4. The solution is filtered with a 0.22 μm filter and kept refrigerated.

Buffer exchange: 2 PD10 desalting columns (Amersham Biosciences) are used for 5 mL of the protein. Total column volume is 3.5 mL, and it is recommended for exchange of no more than 2.5 mL each. Each column is rinsed with no less than 25 mL of 40 mM $NH_4OAc$ buffer to saturate the column with the buffer. Then, 2.5 mL of the anti-Factor VIII in phosphate buffer is inserted into the column followed by additional 1 mL of the $NH_4OAc$ buffer to fill the column. The protein is collected by injecting an additional 2.5 mL of the 40 mM $NH_4OAc$ buffer.

A preferred dialysis cassette is a 1 Pierce, with 3-12 mL total volume, and a MW cutoff of 10,000 Daltons to replace the buffer for 5 mL of the protein. The cassette is hydrated prior to use with deionized $H_2O$, such as by using a 5-10 mL syringe with 18G½ needle. First, air is injected into the cassette to separate the membrane walls. And the sample is injected. Air is withdrawn from the cassette to have a better sample-membrane contact. The float is added on, and the cassette spun at low speed. Each buffer exchange should be at least approximately 10× in volume.

Protein concentration: Protein concentration is determined by measuring absorbance at 280 nm and calibration curve. If needed, the protein can be with the buffer according to the desired working concentration.

The pH of the 10% Poloxamer solution is adjusted with acetic acid to pH6.0 and pH6.1. The 5 mL of the protein is divided into 10 batches of 500 μL. Then, 1000 μL of 10% Poloxamer 188 in 40 mM AA at pH6.0 is added to 5 Eppendorf tubes, and 1000 μL of 10% Poloxamer 188 in 40 mM AA at pH6.1 is added to the other 5 Eppendorf tubes. The solutions are mixed well by gentle vortexing and hand mixing. The solutions should look clear to slightly hazy. The samples are incubated for 1-2 hours (~4 C.) to achieve slow cooling. The samples are cooled with dry ice/ethanol mixture and lyophilized over night, or place into a −80 C. refrigerator; to remove all of the deionized $H_2O$.

Once all the deionized $H_2O$ is removed, 1 mL of $MeCl_2$/5% Acetone is added to the dry samples in each Eppendorf tube. The samples are mixed, and centrifuged at 6000-8000 RPM for 3 minutes. The supernatant is carefully removed from the centrifuge and decanted, and washing is repeated two additional times.

After the last wash is complete, the supernatant is decanted, and additional solvent is removed using low, very gentle $N_2$ flow to avoid suspension of the powder. The dry tubes are placed on the lyophilizer to remove residual solvent, and microspheres of anti-Factor VIII monoclonal antibody are collected.

EXAMPLE 2

This Example provides another procedure for preparation of 500 μl batches of anti-CD34 monoclonal antibody microspheres in Eppendorf tubes:

Preparation of 40 mM Ammonium Acetate Buffer at pH6.0: 40 mM of Ammonium Acetate (AA) buffer is prepared by dissolving 3.08 grains of AA (Spectrum) in 1 liter of deionized $diH_2O$. The AA is readily soluble and forms a buffer solution with a pH~ 6.4. Adjust the pH to pH6.0 with dilute acetic acid.

Preparation of 500 mL of 15% Poloxamer 188 in 40 mM AA Buffer solution: 75 grams of Poloxamer 188 (BASF) are dissolved in 500 mL of 40 mM AA Buffer (as described in step 1, but pH adjustment is not necessary). The dissolution of this quantity of Poloxamer can be carried out in several additions. The final pH is around pH~6.4. The solution is filtered with a 0.22 μm filter and kept refrigerated.

Buffer exchange: 2 PD10 desalting columns (Amersham Biosciences) are used for 5 mL of the protein. Total column volume is 3.5 mL. Each column is rinsed with no less than 25 mL of 40 mM $NH_4OAc$ buffer to saturate the column with the buffer. Then, 2.5 mL of the anti-CD34 in phosphate buffer is inserted into the column followed by additional 1 mL of the $NH_4OAc$ buffer to fill the column. The protein is collected by injecting an additional 2.5 mL of the 40 mM $NH_4OAc$ buffer. A 1 Pierce dialysis cassette with total volume 3-12 mL, and a MW cutoff of 10,000 MW is used to replace the buffer for 5 mL of the protein. The sample is injected. The float is added on, and the cassette is used to spin at low speed.

Protein concentration is determined by measuring absorbance at 280 nm and using a calibration curve. If needed, the protein is diluted with the buffer according to the desired working concentration. The working concentration for this Example was determined as 1.8 mg/ml (final concentration is 0.9 mg/ml).

The pH of the 15% Poloxamer solution is adjusted with acetic acid to pH5.8 and pH5.9. The 5 mL, of the protein is divided into 10 batches of 500 μL 500 μL of 15% Poloxamer 188 in 40 mM AA is added at pH5.8 to 5 Eppendorf tubes, and 500 µL of 15% Poloxamer 188 is added in 40 mM AA at pH5.9 to the other 5 Eppendorf tubes.

The solutions are mixed well by gentle vortexing and hand mixing, with the solutions looking clear to slightly hazy, the samples are incubated for 1-2 hours in the 'fish bowl' (~4 C.), effecting slow cooling.

The samples are rapidly frozen in an ice/ethanol mixture and lyophilized over night to remove all of the deionized $H_2O$, or the samples are placed in a −80 C. refrigerator. Once all the deionized $H_2O$ is removed, 1 mL of $MeCl_2$/5% Acetone is added to each Eppendorf tube, followed by mixing well and centrifuging at 6000-8000 RPM for 3 minutes. The supernatant is decanted and the washes are repeated two additional times.

After the last wash is complete, the supernatant is decanted, and additional solvent is removed using low and gentle $N_2$ flow. The almost dry tubes are placed on the lyophilizer to remove residual solvent, and microspheres of monoclonal antibody are collected.

EXAMPLE 3

The Example describes preparation of anti-Factor VIII monoclonal antibody microspheres with Poloxamer as solvent and microsphere formation under cooling. Anti-Factor VIII monoclonal antibody in 40 mM phosphate buffer at pH 7.0 and at a concentration of 5.3-5.5 (no sodium chloride) was provided by Baxter Healthcare Corporation (Bioscience Division, Hayward, Calif.). Anti-Factor VIII monoclonal antibody is a murine monoclonal antibody with a molecular weight of approximately 150 kD, and is used for purification purposes. 5 mL of this monoclonal antibody at concentration of 5.3 mg/mL were filtered through 0.22 µm and dialyzed against 40 mM ammonium acetate buffer pH 6.5 using dialysis cassette. Protein concentration was determined by measuring absorbance at optical density of 280 nm. A 10% solution of Poloxamer 188 NF (Lutrol F68) available from BASF Corporation (Florham Park, N.J.) was prepared at pH 6.0 and filtered with 0.22 micron filter. Ammonium acetate was provided by Spectrum Chemicals (Gardena, Calif.). A dialysis cassette SLIDE-A-LYZER®, molecular weight cutoff of 10,000 and sample volume 3-12 mL was provided by Pierce (Rockford, Ill.). Aliquots of 0.5 mL of the monoclonal antibody solution were inserted into twenty 1 mL microfuge tubes. 1 mL of 10% Poloxamer solution was added to each tube containing 0.5 mL of the anti-Factor VIII (at 5.3 mg/mL), and the solution was mixed gently at room temperature and incubated at 29° C. for one-half hour.

Then, the solutions were incubated at 4° C. for 1 hour. During cooling, the clear solution became opaque as microspheres containing a monoclonal antibody were formed. The yield of protein incorporation into microspheres was then determined in the following way: an aliquot of the microsphere suspension was removed, the microspheres were separated from the solution by centrifugation, and the protein concentration in the supernatant was determined by measuring absorbance at optical density of 280 nm. Following incubation, the tubes were flash-frozen and lyophilized. After lyophilization, the dry powder contained the anti-Factor VIII monoclonal antibody microspheres and poloxamer.

Figure 2:
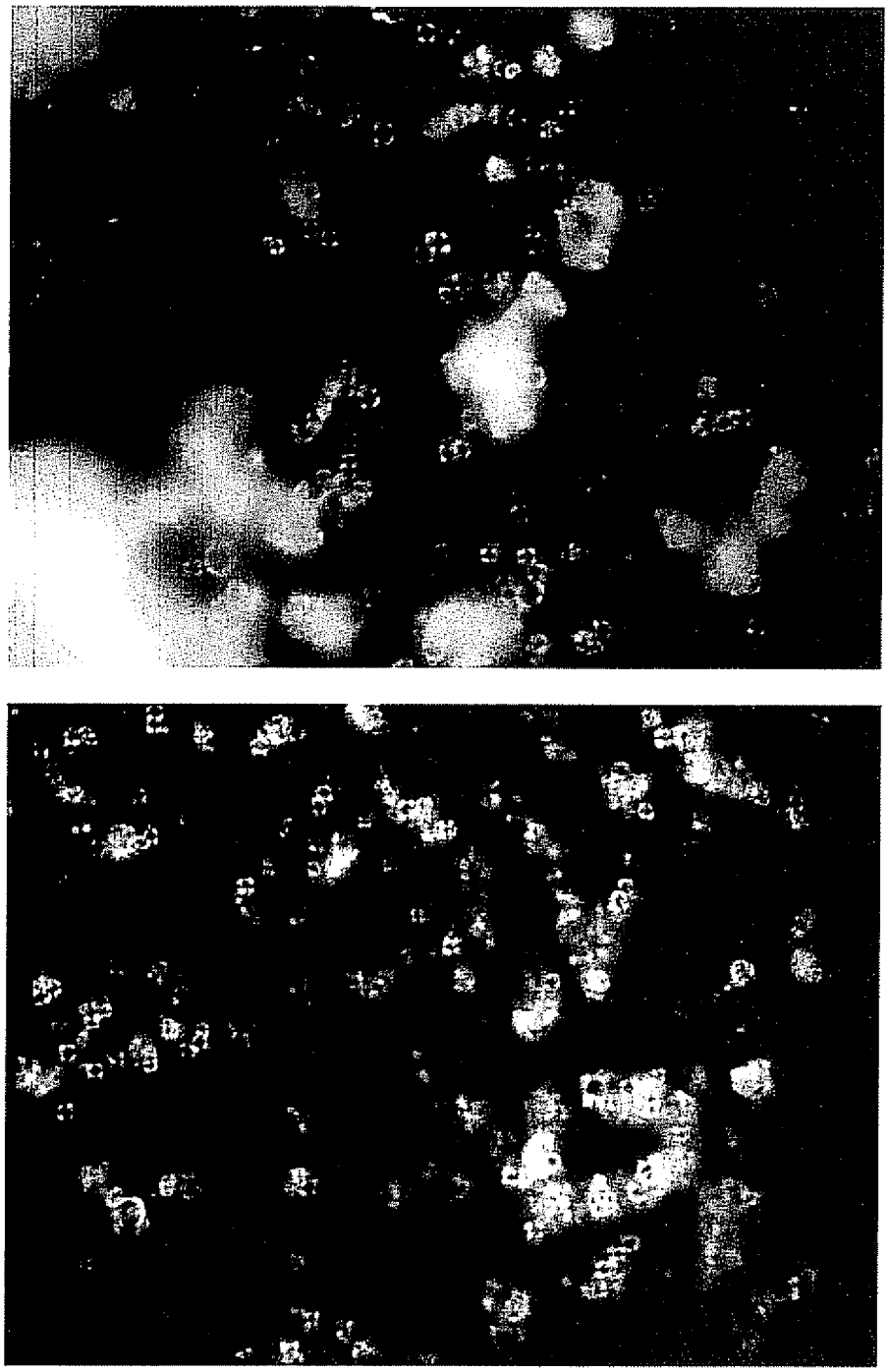
FIG. 2 provides polarized optical microscope images of anti-Factor VIII monoclonal antibody microspheres prepared as described in Example 3.

The poloxamer was removed by the addition of 1 mL of a solution of 95% methylene chloride and 5% acetone to each tube, centrifugation and removal of the supernatant. The washing procedure was repeated three times. The wet pellets were dried using nitrogen gas, and residual solvent was removed using vacuum. The dry power was examined under light microscope. The light microscope images (FIG. 1) and polarized light microscope images (FIG. 2) show spherical particles in the size range of 0.5-5 microns. The samples were sent to SEM (Hitachi S4800, Electron Microscopy Center, Northeastern University, Boston Mass.).

Figure 3:
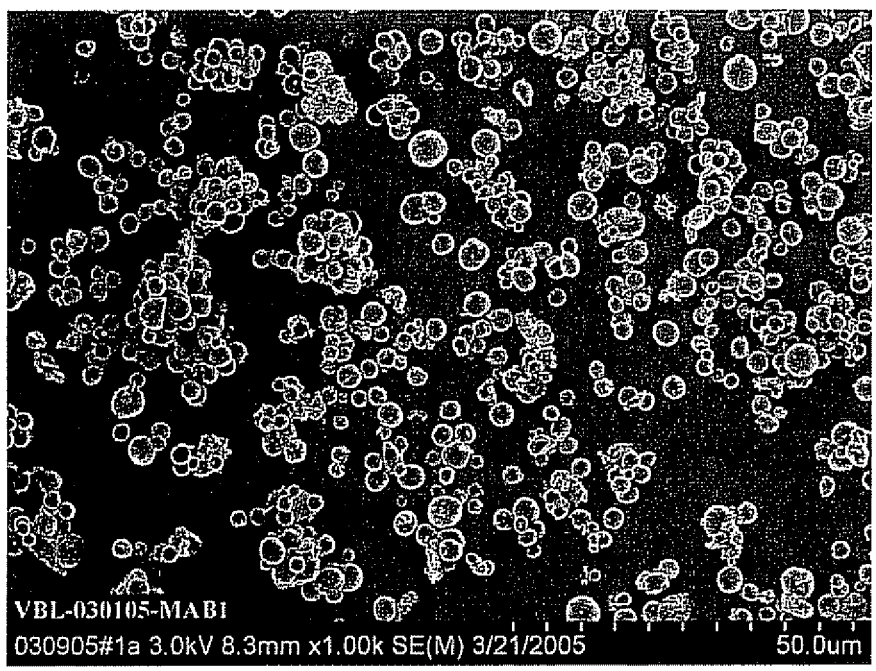
FIG. 3 provides scanning electron micrographs of anti-Factor VIII monoclonal antibody microspheres viewed as described in Example 3.
Figure 3:
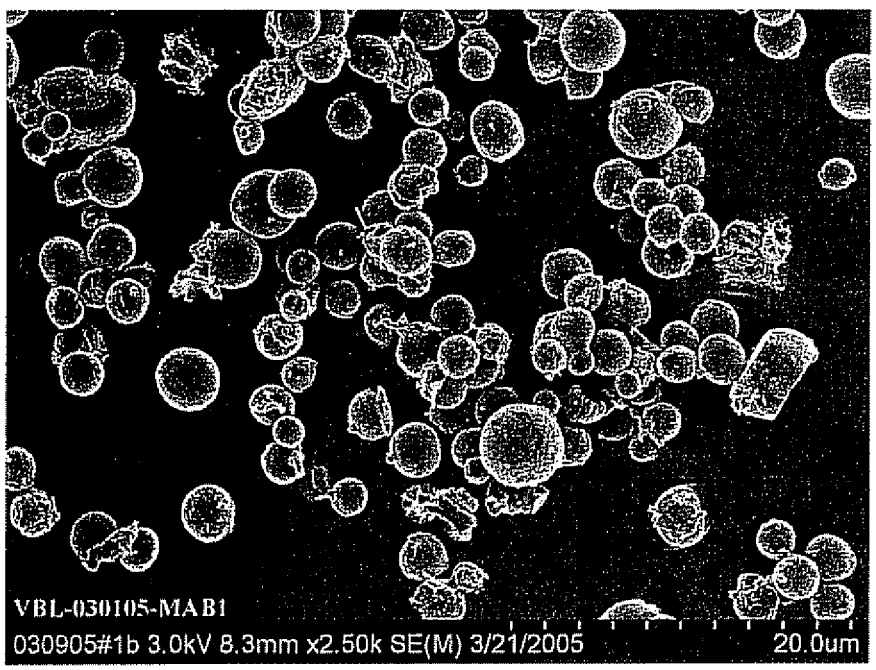

An anti-Factor VIII antibody microsphere sample was attached to the SEM specimen mount using a double-sided conductive carbon adhesive tab, A thin (10-15 nm) conductive layer of Platinum/Palladium 80:20 was applied to the sample via evaporation using a Denton DV-502 vacuum evaporator. The sample was then imaged and digitally recorded on a Hitachi S-4800 Field Emission SEM using an accelerating voltage of 2-3 kV. Scanning electron micrographs (FIG. 3) show spherical particles in the size range of 0.5-6 microns.

When a polarized light passes through an isotropic sample, the sample will have no effect on the polarized light regardless of how the sample is oriented, since all crystal axes are completely equivalent. This effect is known as complete or isotropic extinction, and it occurs for crystals that have a high degree of symmetry, such as cubic systems. Noncrystalline, amorphous samples yield the same behavior. The polarized optical microscope images show the microspheres as dark circles surrounded by a bright halo. These images are independent of the sample's orientation and indicate its spherical shape and amorphous structure.

EXAMPLE 4

This Example shows gel electrophoresis of anti-factor VIII monoclonal antibody microspheres prepared according to Example 3. Tris-Acetate gel, 3-8%, 1.5 mm×10 wells, Tris-Acetate SDS running buffer, NuPage LDS sample buffer, Mark 12 molecular weight Standard, and SIMPLYBLUE SAFESTAIN® drying solution were provided by Invitrogen (Carlsbad, Calif.). Gel electrophoresis is a widely-used analytical technique for the separation and characterization of proteins and peptides, and for the estimation of the molecular weight of protein.

Anti-Factor VIII monoclonal antibody microspheres were prepared according to Example 3 and dissolved in phosphate buffer saline, pH 7.4, at 37° C. 40 µl of three different batches were run in parallel 40 µl of the native anti-Factor VIII solution were run in parallel as a control. For the electrophoresis, the running time was 1 hour, and voltage was 150 mV.

Figure 4:
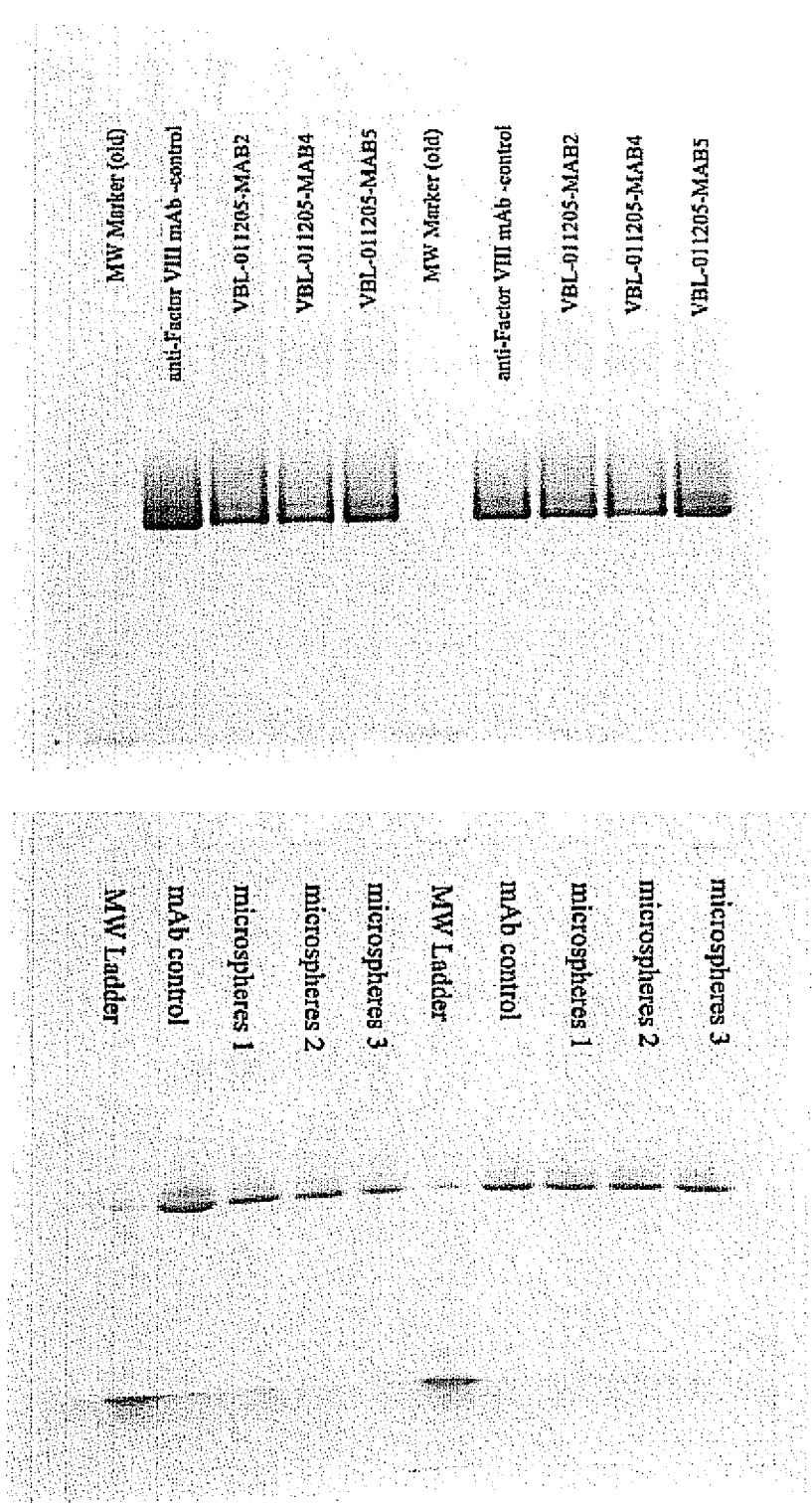
FIG. 4 gives gel electrophoresis images of anti-Factor VIII monoclonal antibody (starting material and dissolved microspheres) as described in Example 4.

FIG. 4 presents two gel images showing that the dissolved monoclonal antibody (released from the microspheres) migrated similarly in the gel when compared with the native monoclonal antibody. All samples migrated to the 150 kD molecular weight marker, which indicates that the protein size has not been changed as a result of the formulation. Stain intensity also was similar, and there were no stains in the gel wells, which indicate that molecular aggregation was minimal.

EXAMPLE 5

This Example describes preparation of anti-factor VIII monoclonal antibody microspheres with PEG/PVP as solvent and microsphere formation under heating. Anti-Factor VIII monoclonal antibody in 40 mM phosphate buffer (no sodium chloride) of Baxter Healthcare Corporation (Bioscience Division, Hayward, Calif.) was formed into microspheres. A 25% PEG/PVP (w/v) solution in 10 mM sodium acetate buffer and pH5.6 was prepared, using polyethylene glycol (PEG) 3350 Daltons, polyvinyl pyrrolidone (PVP), 40,000 Daltons, and sodium acetate, available from Spectrum Chemicals (Gardena, Calif.).

400 μl of 25% PEG/PVP solution were added to 800 μl of the anti-Factor VIII monoclonal antibody solution at a concentration of 5.3 mg/mL at room temperature. The solution was mixed and incubated at 65° C. for one-half hour. Following incubation at 65° C., the solution was rapidly cooled down (quenched) by incubation in cold water to approximately 20° C. Upon cooling, the clear solution became turbid as microspheres comprised of monoclonal antibody were formed. The suspension was centrifuged and the supernatant was removed. Excess PEG/PVP was removed by washes with deionized water.

Figure 5:
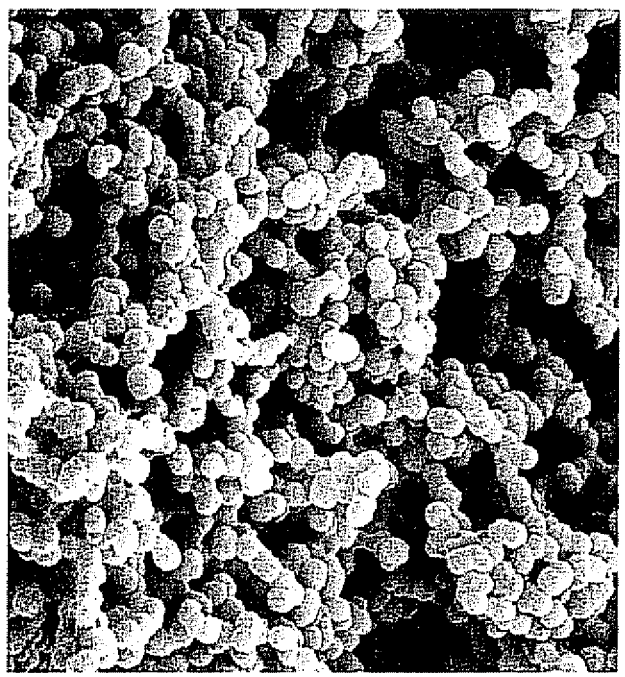
FIG. 5 gives scanning electron micrographs of anti-Factor VIII monoclonal antibody microspheres viewed as described in Example 5.

FIG. 5 presents a scanning electron microscope image of microspheres prepared according to the procedure of this Example. A sample of the microspheres was prepared and analyzed by AMRAY AMR-1000 scanning electron microscope (Electron Microscopy Center, Northeastern University, Boston, Mass.). The sample was taped onto a carbon tab using carbon-based adhesive, and mounted on the SEM specimen position. The sample was coated with Platinum/Palladium 80:20 thin coat under vacuum. The scanning electron micrographs presented in FIG. 5 show spherical particles in the size range of 1-3 μm.

Figure 6:
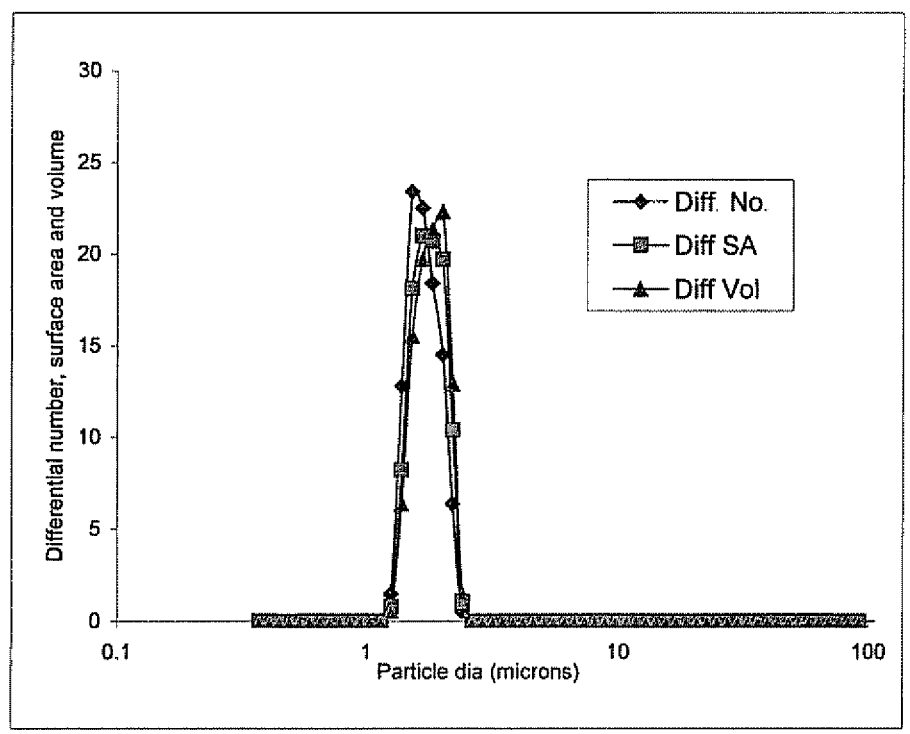
FIG. 6 reports particle size distribution by number, surface area and volume distribution of anti-Factor VIII monoclonal antibody microspheres as described in Example 5.

Particle size distribution by laser light scattering (Beckman Coulter LS 230, Miami Fla.) was conducted on an aqueous suspension of microspheres prepared according to this Example. The distribution of the particle size was narrow, with more than 90% of the particles being smaller than 2 μm. In addition, particle size distribution by number, by surface area, and by volume were superimposed, which indicates that all particles were of approximately the same size with no apparent aggregates. See FIG. 6.

EXAMPLE 6

In this Example, anti-CD34 monoclonal antibody microspheres were prepared with a Poloxamer solvent, and cooling was used for microsphere formation. Anti-CD34 is a murine IgG1 Lambda monoclonal antibody with molecular weight of approximately 146 kD. This monoclonal antibody is used for extra-cellular therapy, such as stem cell selection, in conjunction with the Isolex® 300 and Isolex® 300i Magnetic Cell Selection System (Baxter Healthcare Corporation), Stem cell selection system and treatment is indicated for processing autologous peripheral blood progenitor cell (PBPC) products to obtain a CD34+ cell enriched population intended for hematopoietic reconstitution after myeloablative therapy in patients with CD34-negative tumors.

Anti-CD34 monoclonal antibody in 0.02M sodium phosphate buffer with 0.15M sodium chloride and 0.001% Tween 80, at pH 5.5 and at a concentration of 2.3-2.5 mg/mL, was provided by Baxter Healthcare Corporation (Bioscience Division, Hayward, Calif.). 5 mL of the monoclonal antibody at a concentration of 2.2 mg/mL were filtered through 0.22 μm and dialyzed against 40 mM ammonium acetate buffer, pH 6.0. A 15% solution of Poloxamer 188 NF (Lutrol F68), available from BASF Corporation (Florham Park, N.J.), the solution being at pH 6.0, was prepared and filtered with 0.22 μm filter. Ammonium Acetate was provided by Spectrum Chemicals (Gardena, Calif.). A dialysis cassette SLIDE-A-LYZER®, molecular weight cutoff of 10,000 and sample volume 3-12 mL was provided by Pierce (Rockford, Ill.). Aliquots of 0.5 mL of the monoclonal antibody solution were inserted to twenty 1 mL microfuge tubes. 0.5 mL of the 15% Poloxamer solution was added to each tube containing 0.5 mL of the anti-CD34, at 2.0 mg/mL and the solution was mixed gently at room temperature and incubated at 29° C. for one-half hour.

Then, the solutions were incubated at 4° C. for 1 hour. During cooling, the clear solution became opaque as microspheres comprised of monoclonal antibody were formed. The yield of protein incorporation into microspheres was then determined in the following manner: an aliquot of the microsphere suspension was removed, the microspheres were separated from the solution by centrifugation, and protein concentration in the supernatant was determined by measuring absorbance at optical density of 280 nm. Following incubation, the tubes were flash-frozen and lyophilized. After lyophilization, the dry powder contained the anti-CD34 monoclonal antibody microspheres and poloxamer.

Figure 7:
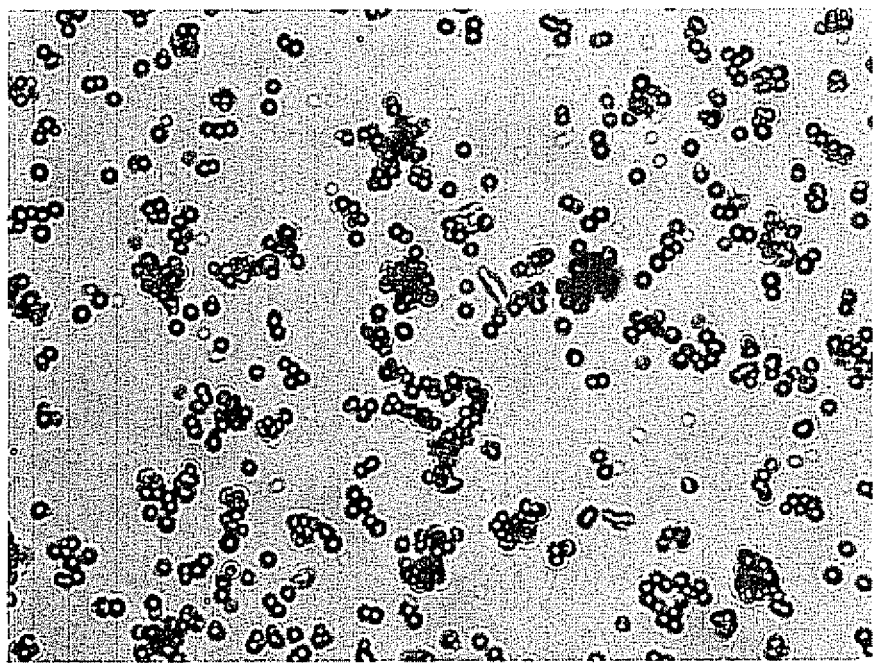
FIG. 7 provides optical microscope images of anti-CD34 monoclonal antibody microspheres prepared as described in Example 6.
Figure 7:
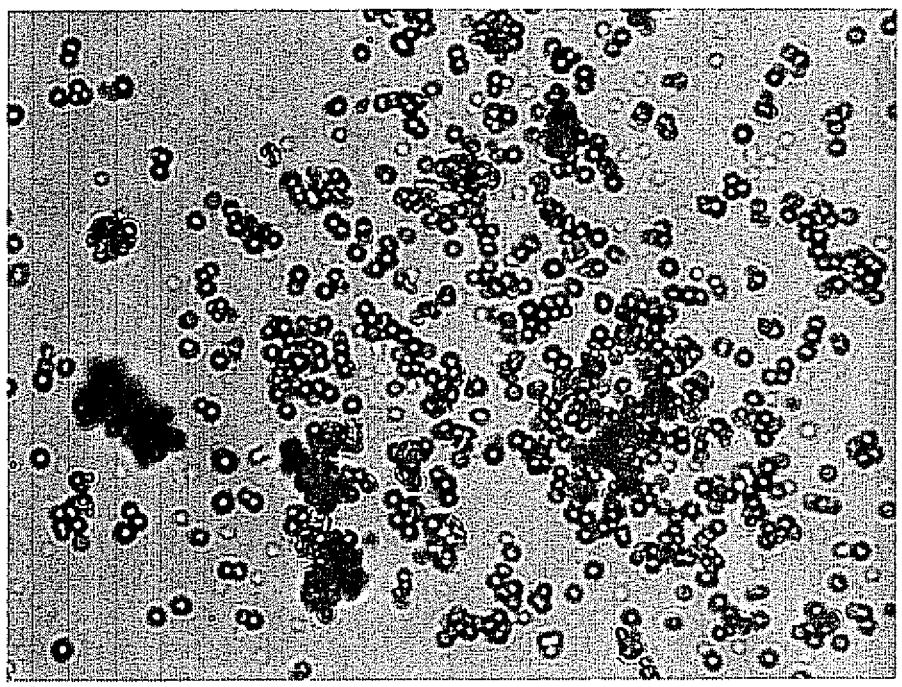
Figure 9:
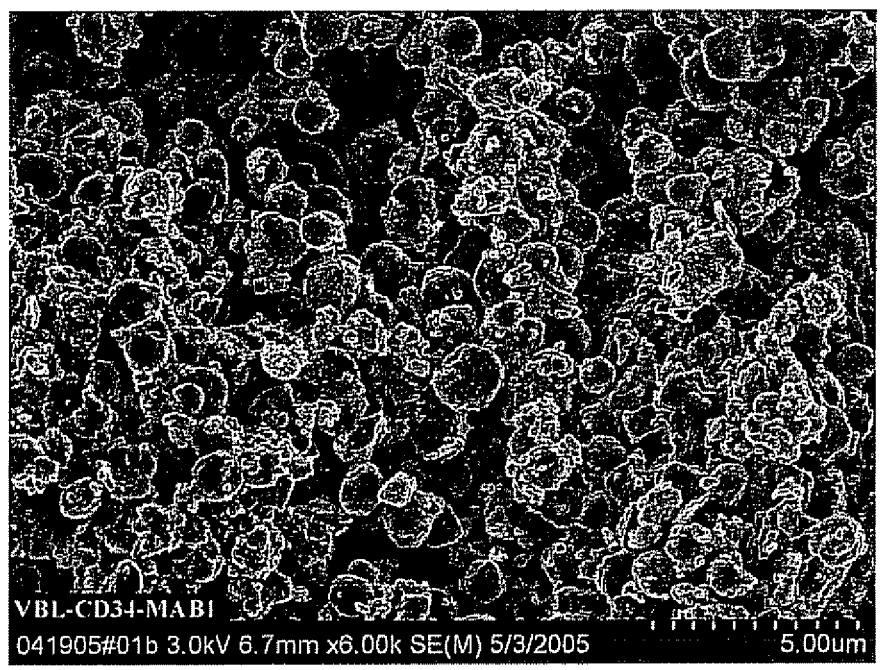
FIG. 9 is a scanning electron micrograph of anti-CD34 monoclonal antibody microspheres prepared as described in Example 6.

The poloxamer was removed by the addition of 1 mL of a solution of 95% methylene chloride and 5% acetone to each tube, followed by centrifugation and removal of the supernatant. The washing procedure was repeated three times. The wet pellets were dried using nitrogen gas, and residual solvent was removed using vacuum. The dry power was examined under light microscope and samples were sent to SEM. Light microscope images (FIG. 7) show spherical particles in the size range of 0.5-5 microns. Scanning electron micrographs of anti-CD34 monoclonal antibody microspheres were viewed as described in Example 5, above (FIG. 9).

Figure 10:
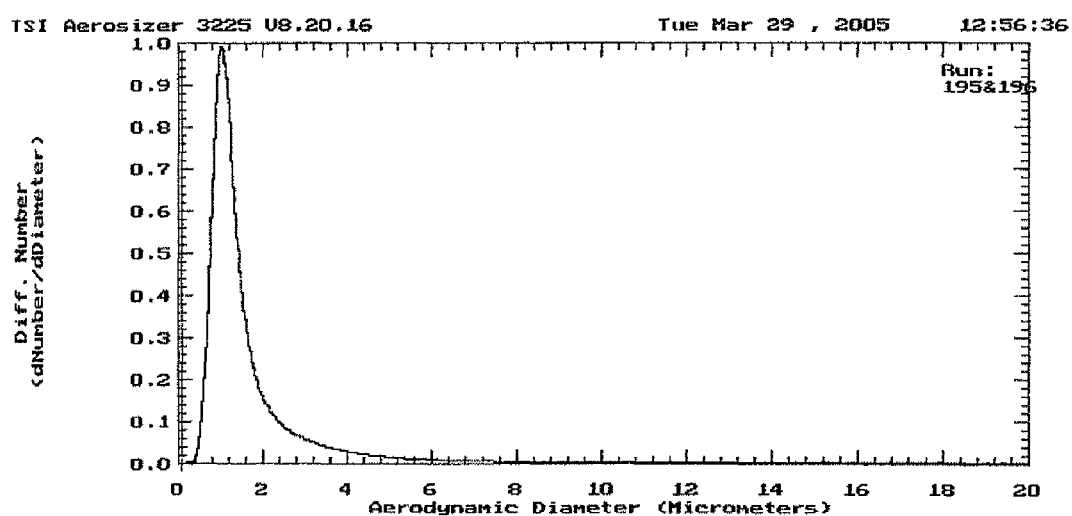
FIG. 10 reports particle size distribution by number distribution of anti-CD34 monoclonal antibody microspheres prepared as described in Example 6.

Particle size distribution by aerodynamic time-of-flight measurement (TSI Aerosizer) was conducted on 5 mg dry powder of anti-CD34 monoclonal antibody microspheres prepared according to this Example. The distribution of the particle size by number was narrow, with mean size aerodynamic diameter of 1.3 μm, and 95% of the particles were smaller than 3.6 μm (FIG. 10).

EXAMPLE 7

Conformational stability of the anti-CD34 monoclonal antibody microspheres of Example 6 was also monitored. In conditions as described in Example 6, 1.5 mL of anti-CD34 in 40 mM ammonium acetate buffer, at pH 6.0 and at a concentration of 1.6 mg/mL, were mixed with 1.5 mL of 15% poloxamer in 40 mM ammonium acetate (pH 6.0 at 25° C.). 3 μL of 10 mM solution of fluorescent dye 8-anilinonaphthalene-1-sulphonic acid (ANS) were added, and the solution was gently mixed and transferred to fluorescence cell.

Conformational stability of anti-CD34 antibody was monitored by using intrinsic fluorescence of the protein's tryptophan and tyrosine residues and extrinsic fluorescence of the ANS dye. Formation of particles in the fluorescence cell was followed using detection of the second overtone at 500 nm of elastic scattering of the light excited at 250 nm. The Example was performed using a Cary Eclipse Biomelt fluorescence spectrophotometer equipped with Peltier-thermostated multicell holder accessory. The sample was incubated at 25° C. for 1 minute, heated to 31° C. at the rate 0.06 degrees Celsius per minute, cooled to 2° C. at the rate of 5 degrees Celsius per minute, and incubated at this temperature for 1 hour. Control samples included 10 μM ANS in 40 mM ammonium acetate (pH 6.0), 10 μM ANS in 40 mM ammonium acetate 7.5% poloxamer (pH 6.0), and 0.8 mg/mL anti-CD34 monoclonal antibody with 10 μM ANS in 40 mM ammonium acetate (pH 6.0).

FIG. 12 presents fluorescence monitoring results of the conformational stability of anti-CD34 monoclonal antibody Fluorescence data support that the protein conformation remained intact during microsphere formation.

EXAMPLE 8

According to this Example anti-CD34 monoclonal antibody microspheres were prepared with Poloxamer or PEG/

PVP solvents, and incorporated heating Anti-CD34 monoclonal antibody in 0.02M sodium phosphate buffer with 0.15M sodium chloride and 0.001% Tween 80, at pH 5.5 and at the concentration of 2.3-2.5 mg/mL, was provided by Baxter Healthcare Corporation (Bioscience Division, Hayward, Calif.) Desalting columns, sample volume 2.5 mL, available form Amersham Bioscience (Piscataway, N.J.), were used to dialyze 5 mL of anti-CD34 monoclonal antibody against 40 mM ammonium acetate buffer (Spectrum Chemicals, Gardena, Calif.) at pH 6.3. Protein concentration was determined by measuring absorbance at optical density of 280 nm. Aliquots of 0.5 mL of the monoclonal antibody solution were placed in ten 1 in L microfuge tubes, and 0.3 mL aliquot of 15% Poloxamer 188 NE (Lutrol F68 by BASF Corporation, Florham Park, N.J.) was added to a tube containing 0.5 mL of the anti-CD34, at 2.1 mg/mL, and the solution was mixed gently at room temperature and incubated at 70° C. for one-half hour.

Figure 8:
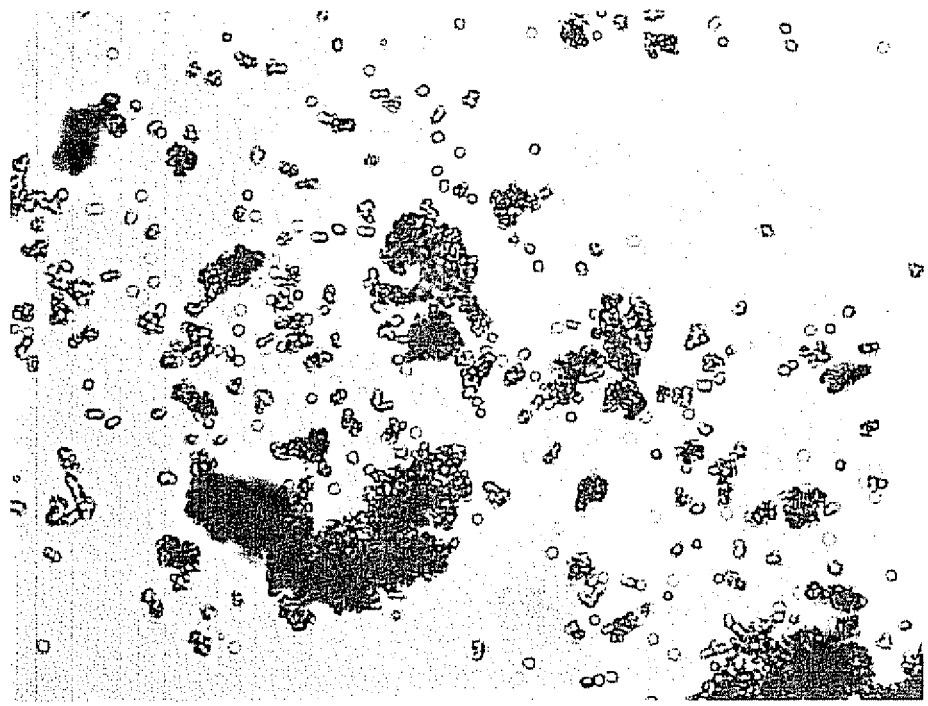
FIG. 8 is an optical microscope image of anti-CD34 monoclonal antibody microspheres prepared as described in Example 8.

Following incubation at 70° C., the solution was rapidly cooled down (quenched) by incubation in cold water to 23° C. Upon cooling, the clear solution became turbid as microspheres comprised of monoclonal antibody were formed. The suspension was centrifuged, and the supernatant was removed. Excess poloxamer was removed by washes with deionized water. An optical microscope image (FIG. 8) show spherical particles in the size range of 0.5-5 µm.

EXAMPLE 9

In this Example, preparation of anti-CD34 monoclonal antibody microspheres is described with PEG/PVP as solvent and microsphere formation under cooling, Anti-CD34 monoclonal antibody in 0.02M sodium phosphate buffer with 0.15 M sodium chloride and 0.001% Tween 80, at pH 5.5 and at the concentration of 2.3-2.5 mg/mL, was provided by Baxter Healthcare Corporation (Bioscience Division, Hayward, Calif.). Polyethylene glycol (PEG) 3350 Da, Polyvinyl pyrrolidone (PVP) 40,000 Da, and sodium acetate were all provided by Spectrum Chemicals (Gardena, Calif.).

25% PEG/PVP solution (pH 5.6) in 100 mM sodium acetate buffer was prepared and filtered through 0.22 µm filter. 5 mL of the monoclonal antibody at the concentration of 2.2 mg/mL was filtered through 0.22 µm filter and dialyzed using a dialysis cassette SLIDE-A-LYZER® (molecular weight cutoff of 10,000 and sample volume 3-12 mL, provided by Pierce (Rockford, Ill.)). The monoclonal antibody was dialyzed against 40 mM ammonium acetate buffer, pH 6.0. Then, 200 µl of 25% PEG/PVP solution (w/v) was added to 500 µl of the anti-CD34 monoclonal antibody at concentration of 2.0 mg/mL and the solution was mixed gently at room temperature and incubated at 29° C. for on-half hour. The process continued as described in Example 6, but for the removal of PEG/PVP, as opposed to poloxamer, by washes with a 95% methylene chloride/5% acetone solution.

EXAMPLE 10

This Example shows X-ray powder diffraction (XRPD) of monoclonal antibody microspheres prepared according to Example 6. High resolution X-ray powder diffraction (XRPD) analyses were acquired using a Shimadzu XRD-6000 X-ray powder diffractometer, equipped with a long fine focus X-ray tube, using Cu Kα radiation (SSCI, West Lafayette, Ind.).

The tube voltage and amperage were set to 40 kV and 40 mA, respectively The divergence and scattering slits were set at 1° and the receiving slit was set at 0.15 mm. Alternately, the divergence and scattering slits were set at 0.5° and the receiving slit was set at 0.15 mm Diffracted radiation was detected by a NaI scintillation detector. A θ-2θ continuous scan at 0.5° per minute (4.8 seconds per 0.02° step) from 1 to 20° 2θ was used. A silicon standard was analyzed to check the instrument alignment. Data were collected and analyzed using XRD-6000 v. 4.1. A low angle standard consisting of an 80:20 mixture of hexatriacontane:silicon was run to demonstrate the instrumental resolution at lower angles for a well-defined 'd' value.

Figure 11:
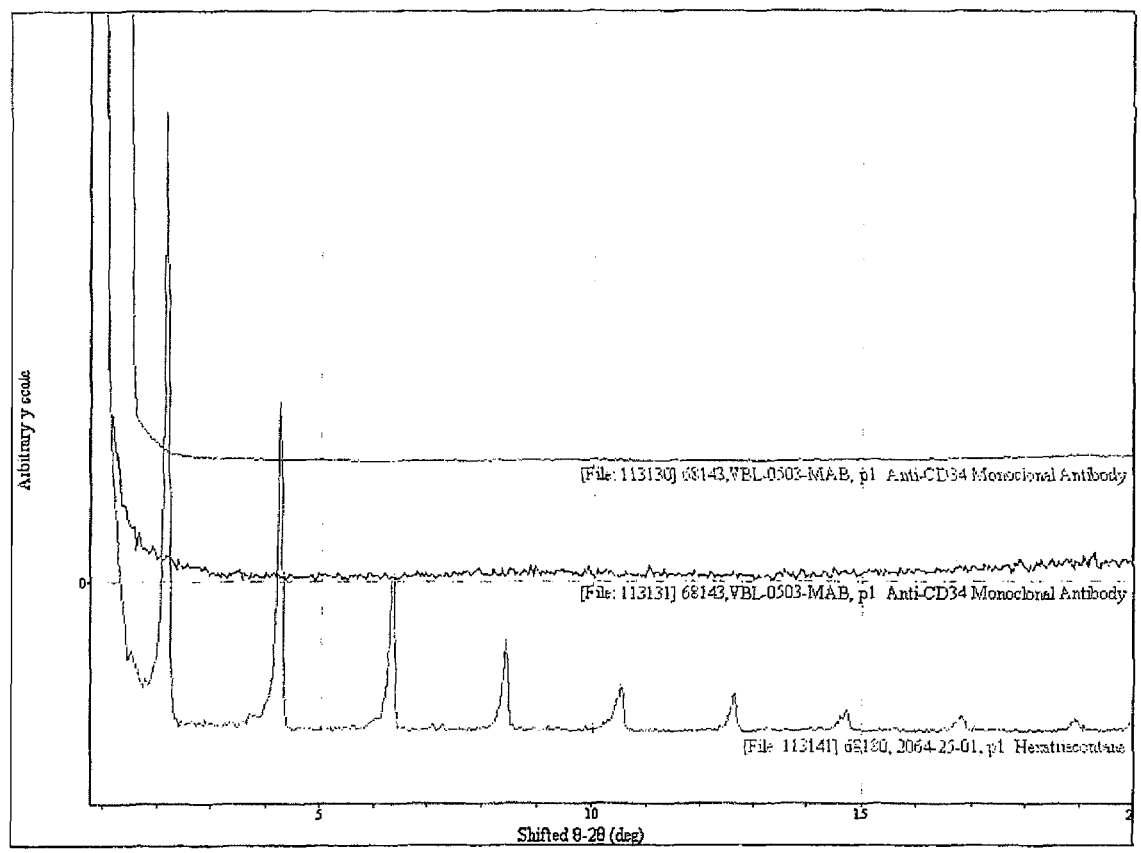
FIG. 11 gives X-ray powder diffraction of anti-CD34 monoclonal antibody microspheres (with 2 slit configuration) and of hexatriacontane:silicon mixture as described in Example 10.
Figure 12:
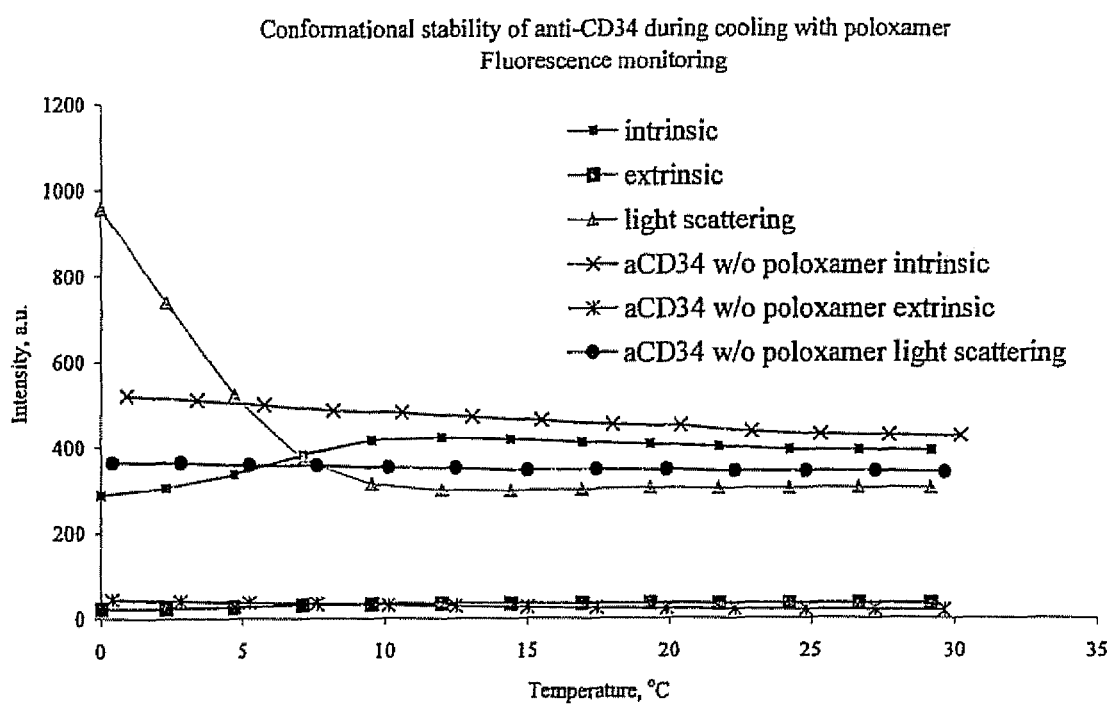
FIG. 12 reports fluorescence monitoring of conformational stability of anti-CD34 monoclonal antibody microspheres during cooling with poloxamer as described in Example 7.

FIG. 11 presents XRPD patterns of the anti-CD34 monoclonal antibody microspheres and of the 80:20 mixture of hexatriacontane:silicon. The XRPD of the hexatriacontane:silicon mixture has distinctive peaks which are indicative of the crystalline state, whereas the XRPD pattern of the antibody microspheres is continuous and has no distinct peaks which is typical of the amorphous, non-crystalline state.

EXAMPLE 11

Anti-CD34 was formulated into microspheres according to the disclosure, generally following Example 2. The microspheres were suspended into a solution of 5% PEG 3350 at the concentrations shown in Table I. A volume of suspended microspheres was aspirated into a syringe and delivered through a 25 Gauge injectability needle into a 4 lb store bought pork shoulder. Each injection was carried out in 20 seconds or less, with no clogging. The results of the syringeability, which in this Example indicates the ability to aspirate the microsphere suspension through the 25 Gauge needle into the syringe and to fully inject the syringe contents into the pork, are recorded in Table I.

TABLE I

| Anti-CD 34 microsphere concentration (mg/mL) | Volume (mL) | Syringeability | Injectability |
| --- | --- | --- | --- |
| 50 | 0.3 | Yes | Yes |
| 200 | 0.15 | Yes | Yes |

The results reported in Table I show that high concentrations of these protein microspheres can be aspirated into a fine (25 Gauge) needle and injected successfully therefrom. This provides an indication of injectability in a subcutaneous environment, through skin and into muscle.

EXAMPLE 12

Insulin microspheres containing greater than 90% weight-by-weight recombinant human insulin were formulated into microspheres according to the disclosure. The insulin microspheres were suspended into a solution of 5% PEG 3350 at the concentrations shown in Table I. One mL of suspended microspheres was aspirated into the syringe and delivered through a 28 Gauge insulin needle into a 10 lb store bought smoked ham. Each injection was carried out in 20 seconds or less, with no clogging. The results of the syringeability, which in this Example indicates the ability to aspirate the microsphere suspension through the 28 Gauge needle into the syringe, and injectability, which in this Example indicates the ability to fully inject the syringe contents into the ham, are recorded in Table II.

TABLE II

| Insulin microsphere concentration (mg/mL) | Volume (mL) | Syringeability | Injectability |
| --- | --- | --- | --- |
| 100 | 1 | Yes | Yes |
| 200 | 1 | Yes | Yes |
| 300 | 1 | Yes | Yes |
| 350 | 1 | Yes | Yes |
| 400 | 1 | Yes | Partially |

The results reported in Table II show that high concentrations of these protein microspheres can be aspirated into a fine (28 Gauge) needed and injected successfully there from into a 10 lb piece of ham. This later step provides a rough indication of injectability in a subcutaneous environment. The 300 mg/ml injection was made with 5.8 newtons of force.

EXAMPLE 13

Insulin microparticles or microspheres are prepared by a general method. A solution buffered at pH 5.65 (0.033M sodium acetate buffer) containing 16.67% PEG 3350 was prepared A concentrated slurry of zinc crystalline insulin was added to this solution while stirring. The insulin concentration in the final solution was 0.83 mg/mL. The solution was heated to about 85 to 90° C. The insulin crystals dissolved completely in this temperature range within five minutes. Insulin small spherical particles started to form at around 60° C. when the temperature of the solution was reduced at a controlled rate. The yield increased as the concentration of PEG increased. This process yields microparticles or microspheres with various size distributions with a mean of 1.4 µm.

The insulin microparticles or microspheres formed were separated from PEG by washing the microspheres via diafiltration under conditions in which the microspheres do not dissolve. The insulin microspheres were washed out of the suspension using an aqueous solution containing $Zn^{2+}$. The $Zn^{2+}$ ion reduces the solubility of the insulin and prevents dissolution that reduces yield and causes microsphere agglomeration.

Figure 14:
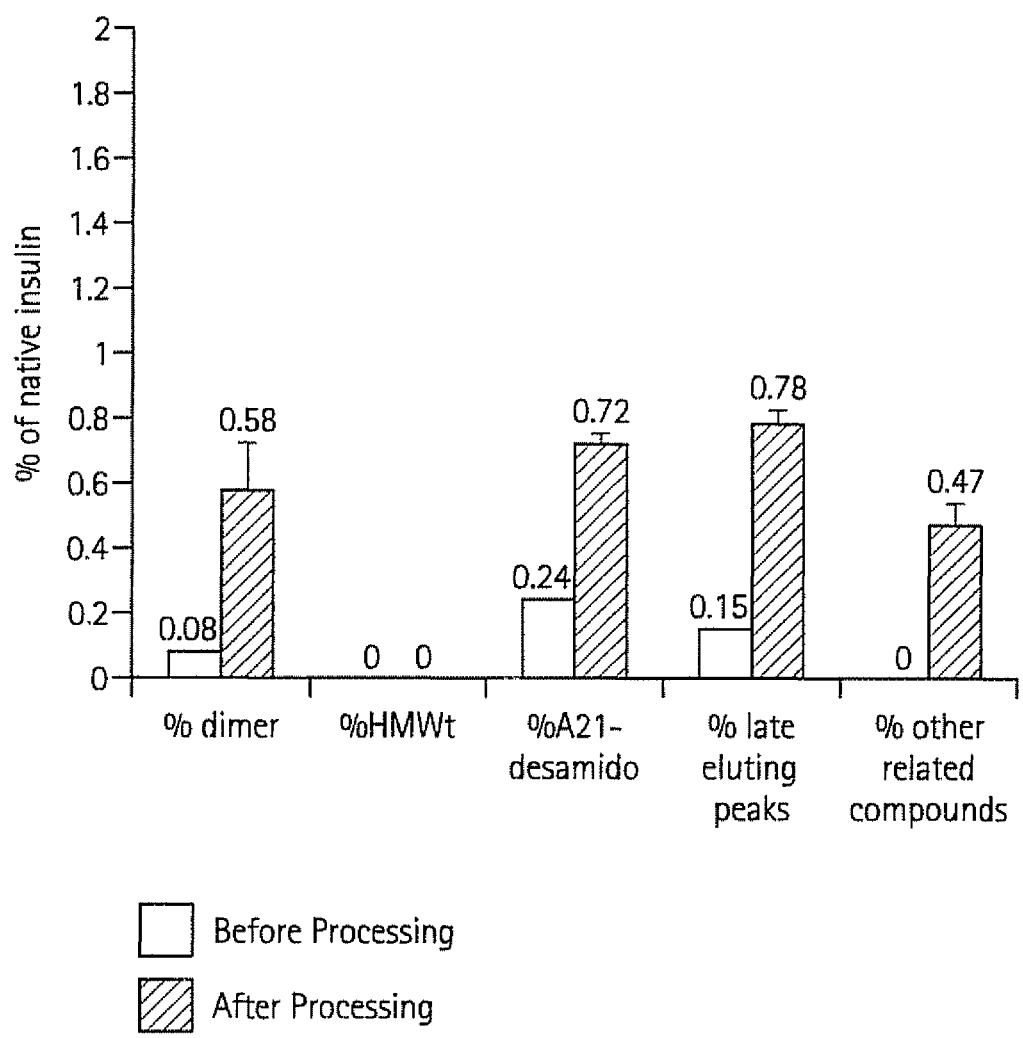
FIG. 14 is an HPLC analysis showing overall maintenance of chemical stability of insulin when prepared into small spherical particles.

FIG. 14 shows the chemical stability of insulin during the microsphere fabrication process HPLC analysis indicated no increase in high molecular weight compounds associated with the process and increases over the starting insulin material in % dimer, % A21 desamido insulin, and % other compounds were within USP limits.

EXAMPLE 14

The present disclosure can also be used to prepare small spherical particles of Alpha-1-Antitrypsin (AAT) which are particularly suitable for the typical syringable delivery route of the disclosure, AAT has a molecular weight of about 44 kDa. This Example reports on jacketed column batch preparation of AAT small spherical particles (10-300 mg scale).

A solution buffered at pH 6.0 with 10 mM ammonium acetate containing 16% PEG 3350 and 0.02% Pluronic F-68 was mixed with a magnetic stirbar in a jacketed beaker and heated to 30° C. The beaker temperature was controlled using a circulating water bath. A concentrated solution of recombinant AAT (rAAT) was added to this solution while stirring and the pH was adjusted to 6.0. The rAAT concentration in the final solution was 2 mg/ml. The rAAT was completely soluble at this temperature in this solution composition. The entire contents of the vessel were transferred to a jacketed column and heated to 25-30° C. The circulating water bath for the column was set to ramp down to −5° C. The column and contents were cooled at approximately 1° C./minute to a temperature of about 4° C. The rAAT small spherical particles formed during the cooling step. The microsphere suspension was frozen in glass crystallizing dishes and lyophilized to remove the water and buffer.

In order to extract PEG from the protein small spherical particles after lyophilization, the PEG/protein cake washed with methylene chloride ($MeCd_2$). Another washing media utilized was methylene chloride:acetone 1:1, or methylene chloride:pentane 1:1. The washing procedure was repeated for a total of 3 times the original volume washes. The final pellet was resuspended in a small volume of acetone or pentane and dried by either direct exposure to nitrogen gas or by rotary evaporation.

EXAMPLE 15

In this Example, AAT small spherical particles (200-2000 mg scale) jacketed vessel batch preparation. This type of preparation was done using the same formulation composition as the jacketed column but capable of accommodating larger volumes and was more suitable for scale-up. At this scale, the formulation was mixed at 75 rpm with an A-shaped paddle style impeller in a jacketed vessel, usually 500-1000 ml, and heated to 30° C. The vessel temperature was controlled using a circulating water bath. Keeping the solution in the same vessel, the water bath source was switched from a 30° C. bath to a 2° C. bath. The vessel and contents were cooled at approximately 1° C./minute to a temperature of 4° C. The rAAT small spherical particles formed during the cooling step. The temperature was monitored using a thermocouple, and when the suspension reached 4° C., it was held close to this temperature for an additional 30 minutes. After the hold step, the small spherical particle suspension was concentrated via diafiltration at around 4° C. to remove approximately 75% of the polymer and volume. The remaining small spherical particle suspension was frozen as a thin layer in a precooled lyophilization tray and lyophilized to remove the water and remaining buffer.

The protein small spherical particles were separated from the remaining dried polymer either by centrifugation with organic solvents (as described in Example 18) or by supercritical fluid (SCF) extraction. For SCF extraction, the dried material was transferred into a high pressure extraction chamber, which was pressurized to 2500 psi (at room temperature) with $CO_2$. Once operating pressure was reached, ethanol was introduced to the inlet fluid stream as a 70:30 $CO_2$:ethanol mix. This super critical fluid dissolved the polymer, leaving the small spherical particles. At the conclusion of the process, the system was flushed of ethanol and slowly decompressed.

EXAMPLE 16

This Example illustrates retention of AAT bioactivity. To determine the specific activity, the rAAT small spherical particles were dissolved in 0.2M Tris-HCl pH 8.0 at room temperature. The resulting solution was analyzed by an assay which measures the capacity of rAAT to inhibit the ability of porcine pancreatic elastase (PPE) to hydrolyze synthetic peptides that contain a p-nitroanilide group at their C-terminus. The same solution of rAAT small spherical particles was then assayed for protein concentration using the Bicinchoninic Acid (BCA) assay. A control rAAT starting material solution was also analyzed in both assays. Because the activity assay was developed to determine the activity based on a concentration of 1 mg/ml protein per sample, the activity value was corrected based on the actual protein concentration as determined by BCA, giving the specific activity value:

$$\frac{\text{activity value for sample}}{\text{actual protein concentration}} = \text{specific activity for sample}$$

Inhibition of Porcine Pancreatic Elastase by rAAT

| Scale | IU/mg small spherical particles | IU/mg control |
|---|---|---|
| 100-300 mg (n = 12, column) | 64.19 ± 5.01 | 64.34 ± 4.95 |
| 200-300 mg (n = 8, vessel) | 62.53 ± 5.29 | 65.87 ± 0.98 |

The specific activity thus demonstrated the retention of bioactivity after fabrication of AAT into small spherical particles.

EXAMPLE 17

This Example describes preparation of humanized monoclonal antibody microspheres with PEG or Poloxamer as solvent and microsphere formation under cooling. A 1 mL solution of 4 mg/mL humanized monoclonal antibody (anti-CD25 monoclonal antibody) in 40 mM ammonium acetate buffer at pH 5.9 was mixed with 1 mL of 30% (w/v) solution of PEG 3350 Da, available from Spectrum Chemicals (Gardena, Calif.) in water. Alternately, the solution was mixed with 1 mL of 30% (w/v) solution of poloxamer 188 NF (Lutrol F68), available from BASF Corporation (Florham Park, N.J.), in water. The mixtures were incubated in a water bath for 10 minutes at 35° C. and then were cooled to 2° C. at a rate of approximately 0.7 degrees Celsius per minute.

The samples were then viewed in the light microscope at 10× and 100× magnification, and showed formation of spherical particles using either polymer. Most of the microspheres appeared to be about 2 microns in diameter, but some were smaller. Few microspheres were larger than 5 microns in diameter.

EXAMPLE 18

This Example illustrates retention of AAT structural integrity. In the particle engineering field, major concerns are the stability of proteins during the fabrication and the storage stability. The main degradation pathways such as oxidation, deamidation and especially aggregation of proteins are believed to be responsible for protein formulation side effects including immunogenicity. Therefore, regulatory concerns require an extremely low level of degradation products in final particle formulations. HPLC, physical chemical characterization such as CD and DSC were utilized to determine whether protein modification occurred during formation.

Circular Dichroism (CD) is the most commonly used method for evaluation of structural changes in a protein subjected to perturbation, or comparison of the structure of an engineered protein to the parent protein. The CD method is assessing protein folding, and protein secondary and tertiary structure.

Secondary structure can be determined by CD spectroscopy in the "far-UV" spectral region (190-250 nm). At these wavelengths, the chromophore is the peptide bond when it is located in a regular, folded environment. Alpha-helix, beta-sheet, and random coil structures each give rise to a characteristic shape and magnitude of CD spectrum. The approximate fraction of each secondary structure type that is present in any protein can thus be determined by analyzing its far-UV CD spectrum as a sum of fractional multiples of such reference spectra for each structural type.

The CD spectrum of a protein in the "near-UV" spectral region (250-350 nm) can be sensitive to certain aspects of tertiary structure. At these wavelengths the chromophores are the aromatic amino acids and disulfide bonds, and the CD signals they produce are sensitive to the overall tertiary structure of the protein Signals in the region from 250-270 nm are attributable to phenylalanine residues, signals from 270-290 nm are attributable to tyrosine, and those from 280-300 nm are attributable to tryptophan. Disulfide bonds give rise to broad weak signals throughout the near-LTV spectrum.

Figure 15:
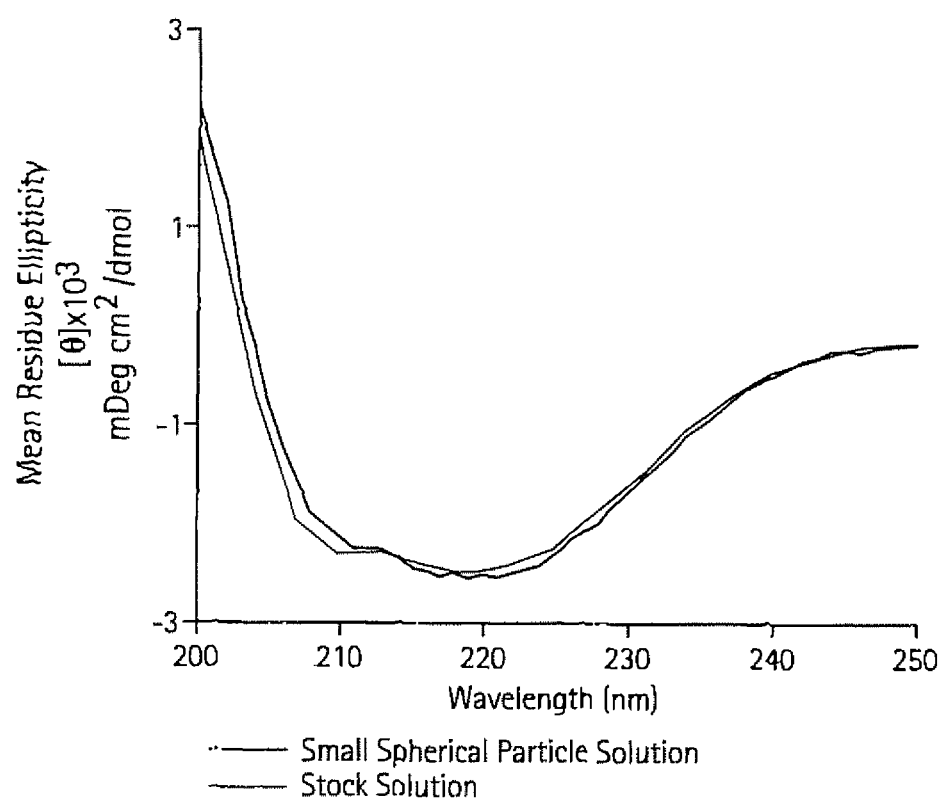
FIG. 15 is a circular dichroism (CD) plot for alpha-1-antitrypsin (AAT).

Far-UV CD spectra of the rAAT stock solution and AAT released from small spherical particles in phosphate buffer (pH 7.4, T=25° C., protein concentration 0.05 mg/mL) are shown in FIG. 15, Each spectrum represents the average of 10 scans.

The far-UV CD spectra are indistinguishable, demonstrating that fabrication of AAT into small spherical particles upon its subsequent release resulted in AAT molecules with a structure identical to that of the starting AAT material.

Small spherical particles were dissolved in 0.2M Tris-HCl at pH 8.0 and analyzed by reverse-phase HPLC. When compared to a control solution of starting rAAT protein, there is no apparent difference in the appearance of the chromatograms.

HPLC system:
HPLC Column—Pheomenex Jupiter, 5 micron, C4, 300 A, 250×4.6 mm
Waters Alliance 2965 Pump/autosampler
Wavelength—280 nm
Injection Volume—75 ul
Gradient of concentration:
Mobile phase 1: 0.1% TFA in water
Mobile phase 2: 0.085% TFA in 90% (c/v) acetonitrile in water
Run time—60 min
Flow rate—1.0 ml/min

EXAMPLE 19

DNase small spherical particles were prepared. DNase has a molecular weight of approximately 38 kDa. Formulation example: A solution of: 0.18 mg/ml DNase (from stock ling/In), 18.2% PEG 3350 (from stock 25%), and 9 mM ammonium acetate, pH 5.15 (from stock 1M) was prepared. This suspension was cooled in the −80° C. freezer and, once frozen, was lyophilized on a manifold lyophilizer, and subsequently washed by centrifugation with $MeCl_2$/acetone.

Figure 16:
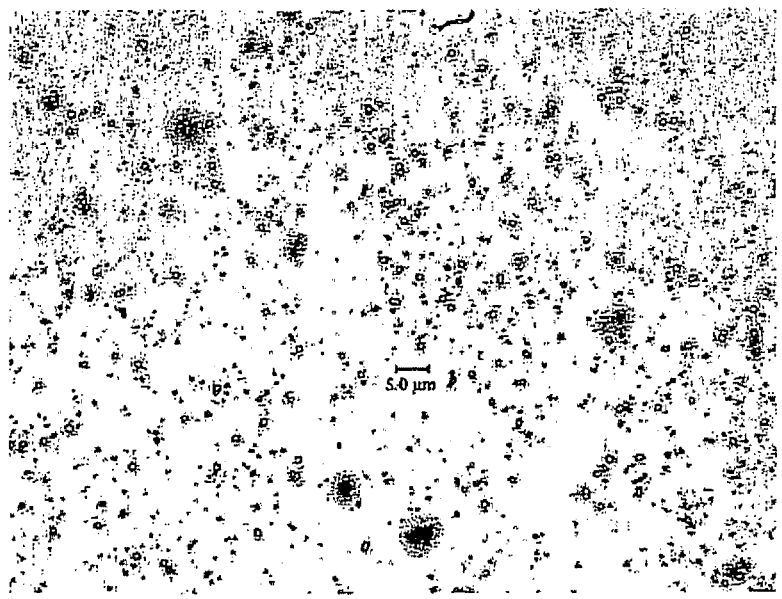
FIG. 16 is a light micrograph of DNase small spherical particles.

Initial concentrations tried were 0.1 mg/ml DNase and 20% PEG 3350. But after trying to cool from 37° C. to 0° C. and not getting a precipitate, another amount of DNase was added to get the above concentrations. This solution was cooled in the −80° C. freezer and, once frozen, was lyophilized on the manifold lyophilizer, then washed by centrifugation with $MeCl_2$/acetone. See FIG. 16.

Activity (Assay for DNase-I using DNA-Methyl Green, purchased from Sigma). The theoretical activity for the starting material is listed as 775 Ku/mg protein. The stock solution was determined to be 0.145 mg/ml protein. This concentration was diluted into 5 ml for a final concentration of 0.0199 mg/ml. The activity should be 775 Ku/mg* 0.0199 mg/ml=15.46 Ku/ml.

$$Kunitz \text{ units/ml of solution} = $$
$$\frac{\Delta A640 \text{ per min of unknown} \times 40 \times \text{dilution factor}}{\Delta A640 \text{ per min of known}}$$
$$Ku/ml = -0.0004 \times 40 \times 1 / -0.0011 = 14.55 \, Ku/ml$$

Compare to theoretical: Small Spherical Particles/theorectical*100%=% activity:

14.55 Ku/ml/15.46 Ku/ml*100%=94.1%

EXAMPLE 20

Figure 17:
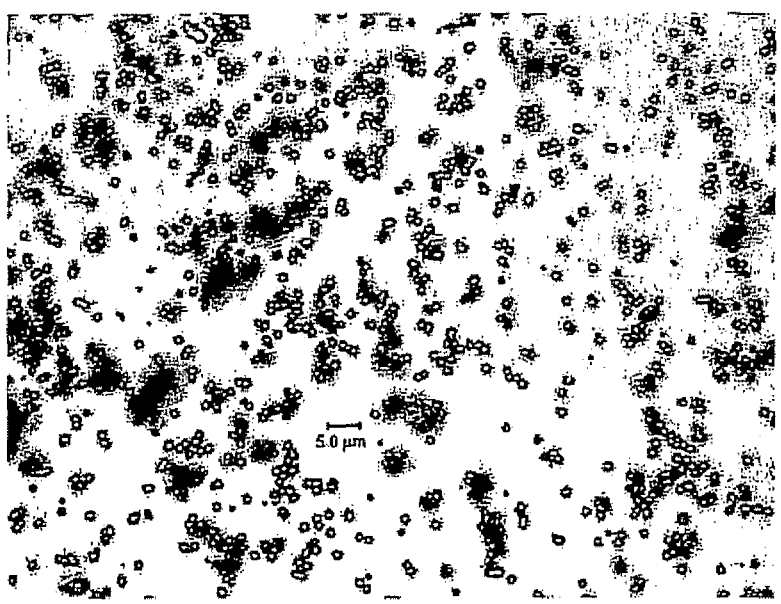
FIG. 17 is a light micrograph of SOD small spherical particles.

Superoxide dismutase (SOD; molecular weight of about 32 kDa) small spherical particles are prepared. A solution of 0.68 mg/ml SOD (from stock 5 mg/ml), 24.15% PEG 3350 (from stock 31.25%), 9.1 mM ammonium acetate (from stock 1M), Final pH 4.99, adjusted with ammonium hydroxide and acetic acid. The solution was cooled from 40° C. to 0° C. over 50 minutes (−0.8° C./min) and precipitation initiated around 25° C. The suspension was flash froze in liquid nitrogen, and lyophilized on a manifold lyophilizer, and subsequently washed by centrifugation with $MeCl_2$/acetone. Small spherical particles were formed (see FIG. 17) and the majority of acetone was removed.

EXAMPLE 21

Subtilisin (molecular weight of about 35,230 Daltons) small spherical particles were prepared using non-polymer phase-separation enhancing agents. The continuous phase of the initial system may contain a non-polymer phase-separation enhancing agent to induce phase separation of a protein during cooling. Subtilisin small spherical particles can be formed according to the present disclosure using a mixture of propylene glycol and ethanol without the use of any polymers. Propylene glycol serves as a freezing point depression agent and ethanol serves as the phase-separation enhancing agent in this system. Propylene glycol also aids in the formation of a spherical shape of the small spherical particles.

A 20 mg/mL subtilisin solution in 35% propylene glycol, 10% Formate, 0.02% $CaCl_2$ was prepared. The 35% propylene glycol—subtilisin solution was then brought to 67% ethanol while mixing. The solution remained clear at room temperature. However, when cooled to −20° C. for one hour, a suspension of particles formed. After centrifugation to collect the particles and washing with 90% ethanol, Coulter Particle Size analysis was performed, with absolute ethanol as the suspension fluid. The particles yielded Coulter results consistent with discrete particles having an average diameter of 2.2 microns and 95% of the particles were between 0.46 and 3.94 microns. Light microscopy evaluation confirmed these results showing substantially spherical particles. SEM analysis of the particles confirmed the Coulter results.

The retention of subtilisin enzyme activity after conversion of subtilisin in solution to subtilisin small spherical particles was confirmed by a colorimetric assay. The theoretical total units of activity for the small spherical particles were calculated by subtracting the total units found in the supernatant (after separation of the subtilisin particles) from the total units of subtilisin assayed in the ethanol-subtilisin-propylene glycol solution prior to cooling. The actual total units found for the subtilisin small spherical particles divided by the theoretical units expressed as a percentage represents the retention of subtilisin activity after particle formation. By this calculation, 107% of the theoretical subtilisin activity was retained after formation of the subtilisin small spherical particles.

EXAMPLE 22

Figure 18:
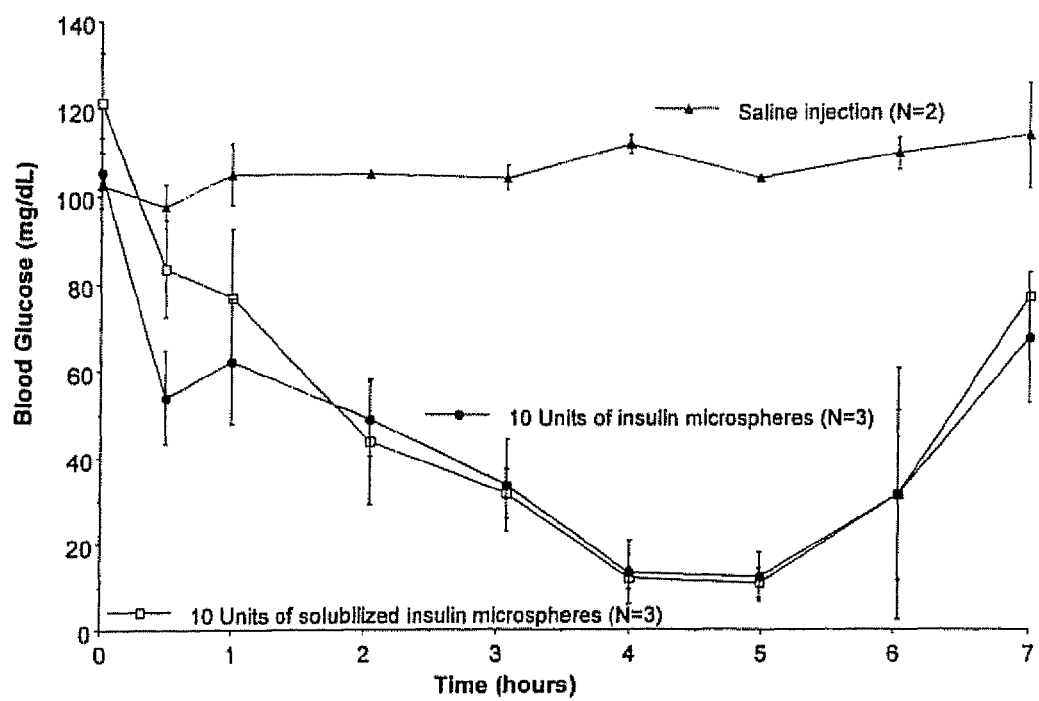
FIG. 18 is a plot of serum glucose concentration levels in rats administered insulin particles of the disclosure or with soluble insulin as described in Example 22.

In this Example, the pharmacodynamic properties of insulin microspheres were examined. Zinc-Insulin microspheres were formulated according to the method of the disclosure. A portion of the preparation of microspheres was suspended in phosphate-buffered saline and vortexed to resolubilize the Zn-insulin. One group of three rats was injected with the Zn-insulin microspheres subcutaneously and a second group of three rats were subcutaneously injected with a solution of the resolubilized Zn-insulin derived from the microspheres. Each animal in both groups received a total of 10.4 units of insulin. A third group of two rats received a saline injection. The blood glucose levels of the rats were monitored after the injections. As shown in FIG. 18, both the group of rats receiving the insulin microspheres and the rats receiving the soluble form of insulin demonstrated suppression of blood glucose levels. Furthermore, both groups of rats showed very similar plots of glucose depression levels over time, indicating the insulin in microsphere form behaves in a very similar manner to the soluble form of insulin.

EXAMPLE 23

This Example describes one method to prepare IVIG microspheres Liquid IVIG (10%, TVR, Lot Number LE12D002) was obtained from Baxter Biosciences (Vienna, Austria). For microsphere manufacture, the liquid IVIG was dialyzed against 100 mM ammonium acetate, pH 6.0, diluted to 2.5 mg/ml, and heated to 50° C. before being mixed with an equal volume of a polymer solution. The polymer solution was 25% PEG8000, 10 mM trehalose, and 100 mM ammonium acetate. The solution was adjusted to pH 5.8 and prewarmed to 65° C. The mixture was immediately placed in a −20° C. freezer to allow the microsphere formation. The microspheres were then concentrated about 10-fold on a diafiltration unit with a 0.22 μm Holofiber membrane (Amersham Biosciences Corp) before lyophilization on a shelf lyophilizer (Advantage, VirTis, SP Industries Inc.). The lyophilized microsphere washed four times with a methylene chloride:acetone (80:20) mixture and dried under nitrogen gas.

EXAMPLE 24

This Example demonstrates the injectability of a 300 mg/mL antibody microsphere suspension in 1 mL injection volume Lyophilized IVIG microspheres were prepared as described in Example 2.3. They were suspended at a concentration of 300 mg/mL in a aqueous based diluent comprised of 20% PEG 300, 5% Poloxamer 188, 10% ethanol and 65% water. One mL of the 300 mg/mL suspension was loaded into a 1 cc syringe fitted with a 26 Gauge needle. The assembly was mounted on an Instrom model 3432 load tester. The rate of suspension delivery from the syringe and 26 G needle was varied from 10 to 30 seconds/mL. The amount of force needed to deliver the suspension was measured in Newtons.

Figure 19:
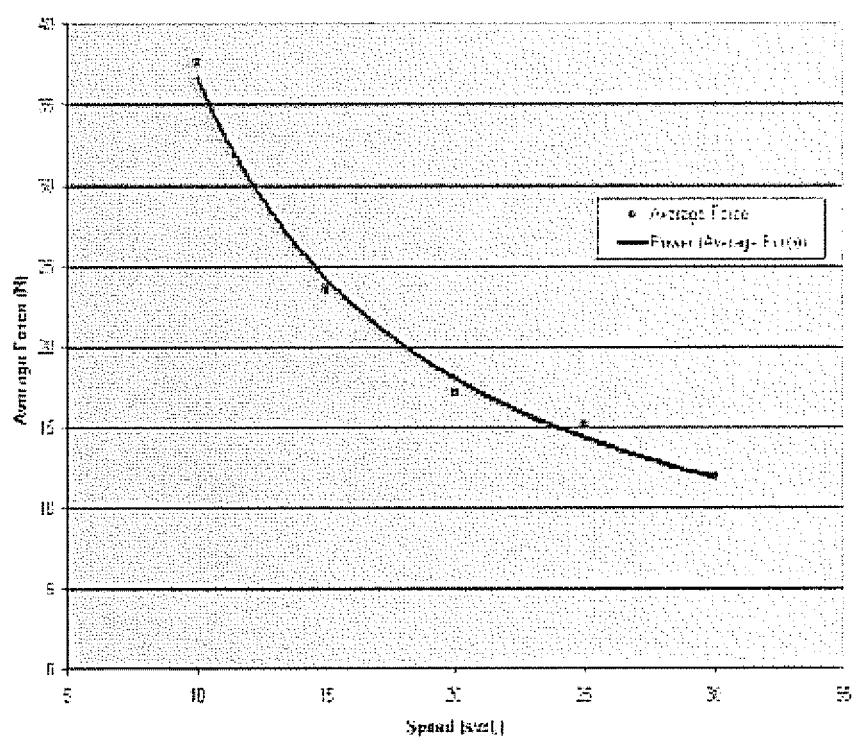
FIG. 19 is a plot showing the injectability of IgG microspheres as described in Example 24.

The data in FIG. 19 show that: a) 300 mg/mL IVIG microspheres were injectable through a 26 G needle, and b) the force needed to inject the microsphere suspension was inversely related to speed of injection. That is, less force was needed the slower the rate of delivery. This Example shows that it is possible to inject high doses of antibody microspheres under clinically acceptable parameters of force, time and needle size.

EXAMPLE 25

Figure 20:
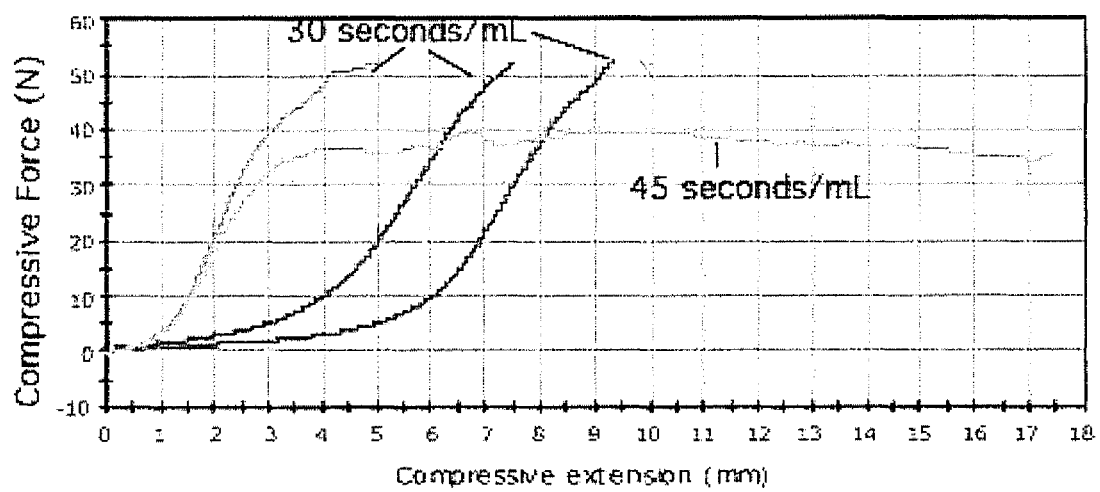
FIG. 20 is a plot showing the injectability of IgG microspheres as described in Example 25.

This Example shows the injectability of a 400 mg/mL antibody microsphere suspension in 1 mL, injection volume. Lyophilized IVIG microspheres were prepared as described in Example 23. They were suspended at a concentration of 400 mg/mL in an aqueous based diluent comprised of 20% PEG 300, 5% Poloxamer 188, 10% ethanol and 65% water. One mL, of the 400 mg/mL suspension was loaded into a 1 cc syringe fitted with a 26 Gauge needle. The assembly was mounted on an Instron model 3432 load tester. The rate of suspension delivery from the syringe and 26 G needle was varied from 30 to 45 seconds/mL. The amount of force needed to deliver the suspension was measured in Newtons. The data in FIG. 20 show that 400 mg/mL IVIG microspheres were injectable through a 26 G needle and that less force was required for injection when the rate of delivery was slowed from 0.30 seconds per mL to 45 seconds per mL. This Example shows that it is possible to inject very high doses of antibody microspheres under clinically acceptable ranges of force, time and needle size.

EXAMPLE 26

Figure 21:
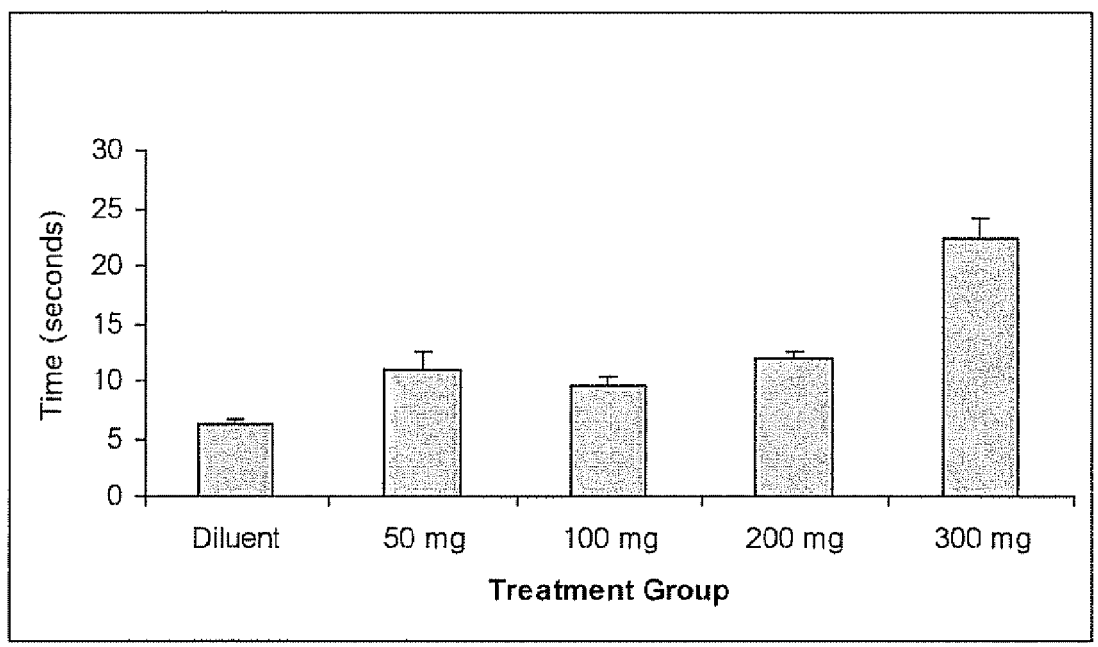
FIG. 21 is a bar graph showing the time required to inject IgG microspheres at various concentrations into Sprague-Dawley rats as described in Example 26.

This Example describes the in vivo injectability of high concentration IVIG antibody microspheres. This study was designed to demonstrate the injectability of different concentrations of IVIG microsphere suspensions, ranging from 50 to 300 mg/ml, into Sprague-Dawley rats with a single subcutaneous injection. Twenty four (24) Sprague-Dawley (SD) rats weighed between 257 and 288 grams. For the injections, rats were randomly assigned to various concentration treatment groups with 3 rats per group. Lyophilized IVIG microspheres were prepared as described as in Example 23, and they were suspended in diluent comprising 20% PEG 300, 5% Poloxamer 188, 10% ethanol and 65% water sterile filtered through a 0.22 micron filter. Each rat was injected subcutaneously with 1 nm of the microspheres through a 26-gauge needle. The time (in seconds) was measured for each injection. The results are summarized in FIG. 21. The data show that the time required to inject the IVIG microspheres ranged from 10 seconds at a concentration of 50 mg/mL and to about 22 seconds at 300 mg/mL. The results from this data indicate the in vivo feasibility of injecting these microspheres at high concentrations. It is possible to inject the microspheres manually with a clinically acceptable amount of force.

EXAMPLE 27

In this Example, the pharmacokinetic properties of IgG formulated into microspheres were compared with the properties of soluble IgG. For these experiments, a purified fraction of IgG antibodies from plasma, termed IVIG, was used Microspheres containing IgG were prepared according to Example 1 using IVIG. One group of rabbits was subcutaneously injected with the IgG-containing microspheres and a second group was subcutaneously injected with soluble IgG, (i.e the IVIG). In addition, a third group of animals received IVIG by intravenous injection. Each animal received 150 mg of IgG per kilogram of body weight. The IVIG solution used for subcutaneous injection was from about 161-178 mg/ml of IgG while the IgG microsphere suspension contained IgG from about 144-173 mg/ml. The intravenous injection of IVIG was performed at 161 mg/ml of IgG.

Following injection of the formulations, serum IgG concentrations were measured with a nephelometric method using the Dade-Behring PROSPEC® system. FIG. 19 shows a plot of the average IgG serum concentration over time for the group of animals subcutaneously administered IgG in microsphere form, the group subcutaneously administered IVIG in soluble form and the group of animals administered IVIG solution intravenously. The data were used to determine pharmacokinetic parameter values for each formulation. In Table III, the calculated values of elimination rate constant (ke), half-life ($t_{1/2}$), clearance (CL) and volume of distribution ($V_d$) are shown for the IVIG solution given intravenously. These values are used for calculations of pharmacokinetic parameters.

TABLE III

| Parameter | IVIG solution (intravenous) |
|---|---|
| N | 8 |
| ke(hr$^{-1}$) | 0.0073 ± 0/0017 |
| T½ | 127.77 ± 23.33 |
| CL(ml/hr/kg) | 0.34 ± 0.06 |
| $V_d$ | 0.0534 ± 0.0074 |

Figure 22:
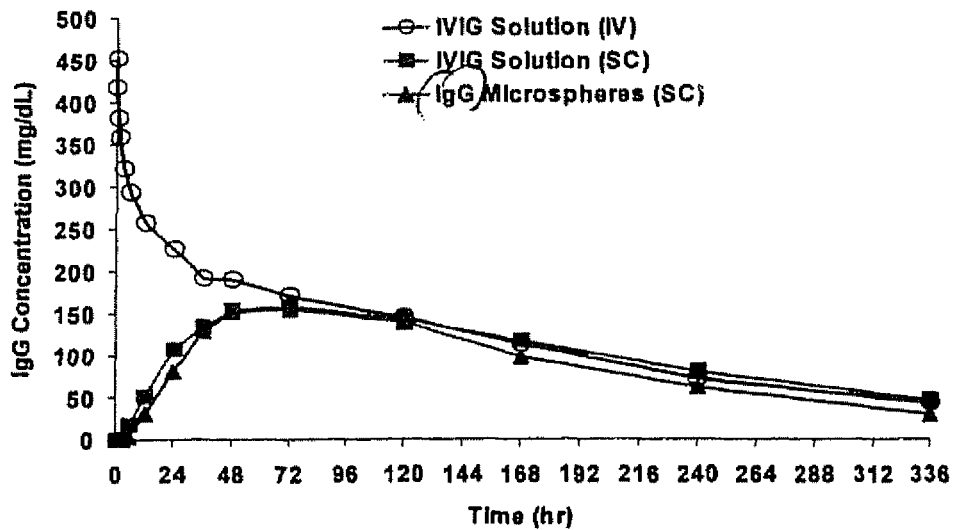
FIG. 22 a and b are a plot of serum concentration levels of IgG in rabbits administered IgG formulated in the particles of the disclosure or with a soluble form of IgG (IVIG) as described in Example 27.
Figure 22:
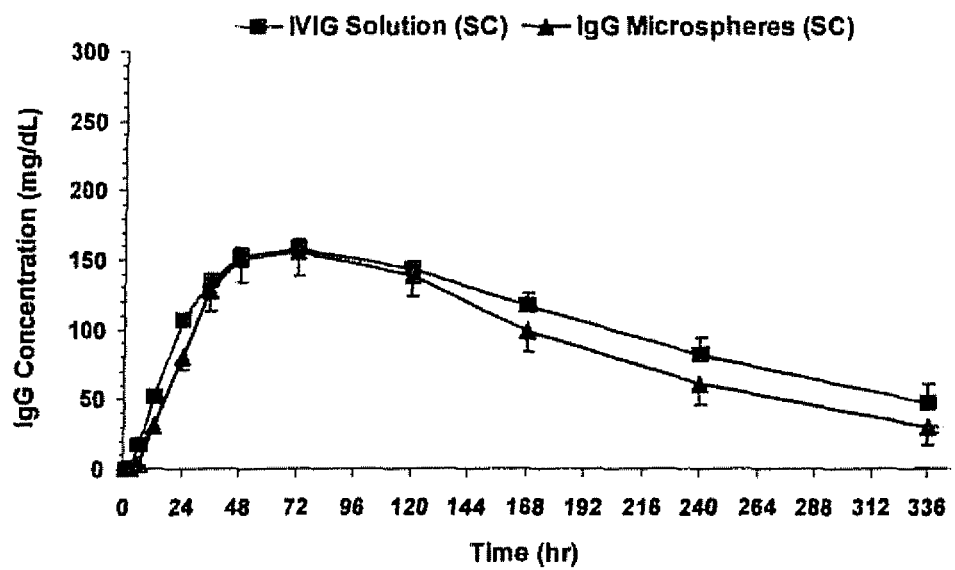

Table IV compares pharmacokinetic parameters for the groups receiving either the IgG-containing microspheres subcutaneously or the IVIG solution subcutaneously. The results are also presented graphically in FIGS. 22-25. The maximal plasma concentration ($C_{max}$) and the time to reach $C_{max}$($T_{max}$) were determined from FIG. 22 and inspection of the data. The area under the serum concentration curve from time 0 to the last measurable concentration at time t ($AUC_{0-t}$) was determined by the trapezoidal rule. $AUC_{0-\infty}$ was determined according to the equation:

$$AUC_{0-\infty} = AUC_{0-t} + C_t/k_e$$

$AUC_{0-\infty}$ values were divided by the dose to obtain a dose-normalized mean $AUC_{0-\infty}$ Relative bioavailability was calculated as the ratio of the dose-normalized mean $AUCO_{0-\infty}$ of the subcutaneously delivered formulations compared to the dose-normalized mean $AUC_{0-\infty}$ for the intravenous formulation.

Figure 23:
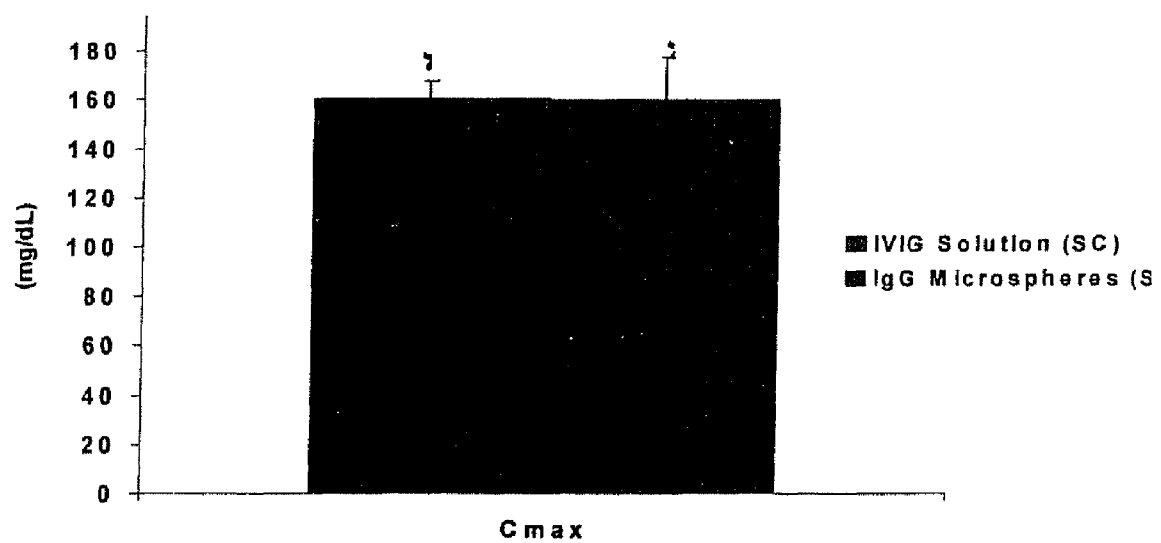
FIG. 23 is graph of $C_{max}$ in animals administered either IgG formulated in the particles of the disclosure or with a soluble form of IgG as described in Example 27.
Figure 24:
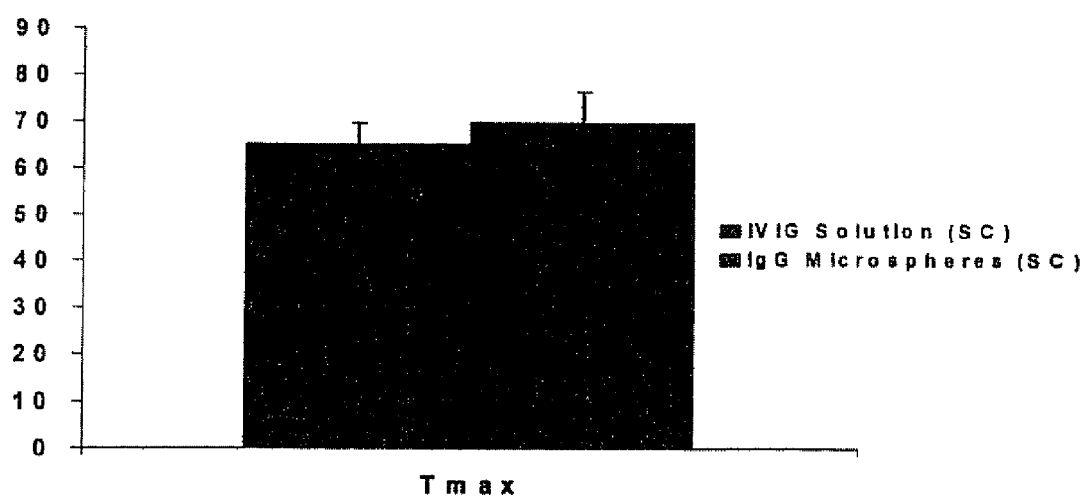
FIG. 24 is graph of $T_{max}$ in animals administered either IgG formulated in the particles of the disclosure or with a soluble form of IgG as described in Example 27
Figure 25:
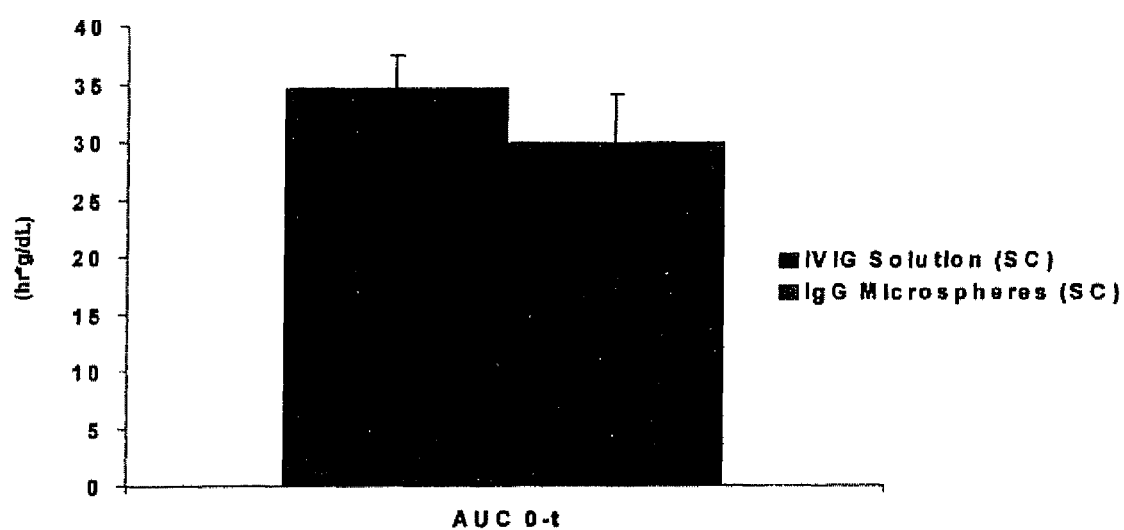
FIG. 25 is graph of Area under the Curve in animals administered either IgG formulated in the particles of the disclosure or with a soluble form of IgG as described in Example 27.

As shown in Table IV and FIGS. 23-25, there are identifiable values that comprise overlapping ranges of values for Cmax, Tmax, and $AUC_{0-t}$ between the group of animals receiving IgG formulated into microspheres and delivered subcutaneously and the group of animals receiving the IVIG solution delivered subcutaneously. Also according to Table IV, there are identifiable values that comprise overlapping ranges of values in $AUC_{0-\infty}$ between the group of animals receiving IgG formulated into microspheres and delivered subcutaneously and the group of animals receiving the IVIG solution delivered subcutaneously. This illustrates that PK values of the microsphere composition of the active agent were the substantially the same as these PK values of the solution composition of the active agent. Thus, formulating the active agent as transforming same into a microsphere composition did not significantly modify these PK values. At the same time, the microsphere composition of the active agent added the benefits of reduced viscosity during subcutaneous delivery through a fine bore needle and enhanced integrity and stability of the active agent in microsphere form when compared with the solution form of the active agent.

TABLE IV

| Parameter | IVIG solution (subcutaneous) | IgG microspheres (subcutaneous) |
|---|---|---|
| N | 7 | 10 |
| Cmax | 160.12 ± 7.34 | 159.45 ± 17.79 |
| Tmax | 65.12 ± 4.43 | 69.60 ± 6.65 |
| AUC 0-t | 34.64 ± 2.83 | 29.84 ± 4.26 |
| AUC 0-∞ | 49.85 ± 9.25 | 39.67 ± 7.85 |
| Frel | 83.35 | 71.81 |

It is to be understood that the embodiments disclosed herein are merely exemplary of the disclosure, which may be embodied in various forms. Therefore, specific details disclosed herein are not to be interpreted as limiting, but merely as a basis for the claims and as a representative basis for teaching one skilled in the art to variously employ the present disclosure in virtually any appropriate manner. The embodiments of the present disclosure which have been described are illustrative of some of the applications of the principles of the present disclosure, and modifications may be made, including those combinations of features that are individually disclosed or claimed herein.

The invention claimed is:

1. An injectable pharmaceutical composition of microparticles comprising substantially amorphous protein microparticles, the composition providing a concentration of at least about 50 mg of said protein in said microparticles per ml of said composition, and wherein a solution of the protein has an identifiable value of a selected pharmacokinetic property when measured in a medium and when administered by a given route, and said composition of microparticles exhibits substantially the same identifiable value of said selected pharmacokinetic property in said medium and when administered by said given route, said pharmacokinetic property selected from the group consisting of $C_{max}$, $T_{max}$, area under the curve (AUC), and relative bioavailability.

2. The composition of claim 1 wherein said protein has a molecular weight of at least about 25,000 Daltons.

3. The composition of claim 1 wherein said protein is an antibody.

4. The composition of claim 1, wherein said protein comprises an antibody selected from the group consisting of monoclonal antibodies, polyclonal antibodies, IVIG, antibody fragments, trap molecules, single chain antibodies, recombinant forms thereof and combinations thereof.

5. The composition of claim 1 wherein said protein is a monoclonal antibody.

6. The composition of claim 1 wherein said protein is insulin.

7. The composition of claim 2 wherein said protein is soluble from at least about 0.5 mg/ml under physiological conditions.

8. The composition of claim 1 wherein said composition provides a concentration of said protein of up to about 500 mg per ml.

9. The composition of claim 1 wherein said composition provides a concentration of said protein from about 100 mg per ml to about 500 mg per ml.

10. The composition of claim 1 wherein said composition provides a concentration of said protein from about 150 mg per ml to about 500 mg per ml.

11. The composition of claim 1 wherein said composition is a subcutaneously injectable composition.

12. The composition of claim 11, wherein a clinically effective amount of said protein microparticles is dispersed in not greater than about 10 mls of said composition.

13. The composition of claim 11, wherein a clinically effective amount of said protein microparticles is dispersed in not greater than about 2 mls of said composition.

14. The composition of claim 11 wherein a clinically effective amount of said composition is injectable in less than about two minutes with a clinically acceptable amount of force.

15. The composition of claim 1, wherein said protein microparticles have an average particle size of not greater than about 50 microns, and the injectable composition passes through an injection needle of 20 gauge or finer.

16. The composition of claim 1 wherein one ml of said composition containing up to about 400 mg/ml of said protein is capable of being injected in about 45 seconds or less with a clinically acceptable amount of force.

17. The composition of claim 1, wherein said microparticles further include an excipient.

18. A microparticle comprising a substantially amorphous antibody wherein a solution of the antibody has an identifiable value of a selected pharmacokinetic property when measured in a medium and when administered by a given route, and said microparticle exhibits substantially the same identifiable value of said selected pharmacokinetic property when measured in the same medium and when administered by said given route, said pharmacokinetic property selected from the group consisting of $C_{max}$, $T_{max}$, area under the curve (AUC), and relative bioavailability.

19. The microparticle of claim 18, therein said antibody is a monoclonal antibody.

20. The microparticle of claim 18, wherein said microparticle is a microsphere having a particle size not greater than about 50 microns.

21. The microparticle of claim 18, wherein said microparticle comprises an antibody selected from the group consisting of a monoclonal antibody, a polyclonal antibody, IVIG, a monoclonal antibody fragment, a trap molecule, a single chain antibody, a recombinant form thereof, and combinations thereof.

22. The microparticle of claim 18, wherein said microparticle further includes an excipient.

23. The microparticle of claim 18, wherein said antibody comprises from about 20 to about 100 weight percent of said microparticle, based on the total weight of the microparticle.

24. A method for administering a protein microparticle composition for an application that requires a selected pharmacokinetic property wherein said pharmacokinetic property is measured in a given medium and administered by a given route, comprising: providing protein molecules that have an identifiable value of a selected pharmacokinetic property within a medium and in soluble form; forming said protein molecules into microparticles; formulating said microparticles for administering the microparticles as said composition; and administering said composition to an individual, whereby said microparticle composition has a value of said selected pharmacokinetic property that is substantially the same as said identifiable value when measured in said medium and when administered by said given route.

25. The method of claim 24 wherein said protein molecules are of a therapeutic agent.

26. The method of claim 24 wherein said protein molecules are of an antibody.

27. The method of claim 24 wherein said protein molecules are of insulin.

28. The method of claim 24 wherein said protein molecules are soluble in the medium from at least about 0.51 mg/ml to about 500 mg/ml.

29. The method of claim 24 wherein said selected pharmacokinetic property is selected from the group consisting of one or more of $C_{max}$, $T_{max}$, area under the curve (AUC), and relative bioavailability.

30. The method of claim 24 wherein said formulating provides said protein molecules in said composition at a concentration of at least about 50 mg/ml.

31. The method of claim 24 wherein said formulating provides said protein molecules in said composition at a concentration of at least about 200 mg/ml.

32. The method of claim 24 wherein said formulating provides said protein molecules in said composition at a concentration of at least about 400 mg/ml.

33. The method of claim 24 wherein said formulating provides said protein molecules in said composition at a concentration of at least about 500 mg/ml.

34. The method of claim 24 wherein said administering is through a needle of 20 gauge or finer.

35. A method of mimicking a pharmacokinetic property of a native form of a protein, comprising: providing native protein molecules that have a selected pharmacokinetic property when administered in native form; forming microparticles from said protein molecules to provide a non-native form of protein molecules; and administering said non-native form of protein microparticles in a manner that mimics said selected pharmacokinetic property.

36. The method of claim 35 wherein said forming provides said protein molecules as a composition and at a concentration of at least about 50 mg/ml.

37. The method of claim 35 wherein said forming provides said protein molecules as a composition and at a concentration of at least about 200 mg/ml.

38. The method of claim 35 wherein said forming provides said protein molecules as a composition and at a concentration of at least about 400 mg/ml.

39. The method of claim 35 wherein said forming provides said protein molecules as a composition and at a concentration of at least about 500 mg/ml.

40. An injectable pharmaceutical composition of microparticles comprising a suspension of substantially amorphous protein microparticles, the composition providing a concentration of at least about 50 mg of said protein in said microparticles per ml of said composition, said protein having a molecular weight of at least about 25,000 Daltons, and wherein an effective amount of said composition is capable of being injected in less than about two minutes with a clinically acceptable amount of force.

41. The composition of claim 40 wherein said effective amount is contained in a dose of about 2 mls or less.

42. The composition of claim 40 wherein said composition provides said protein molecules at a concentration of at least about 300 mg/ml.

43. The composition of claim 40 wherein said composition provides said protein molecules at a concentration of at least about 400 mg/ml.

44. The composition of claim 40 wherein said composition provides said protein molecules at a concentration of at least about 500 mg/ml.

45. The composition of claim 40 wherein one ml of said formulation containing up to about 400 mg/ml of said protein is capable of being injected in from less than about 45 seconds with a clinically acceptable amount of force.

46. A method for administering protein molecules in microparticle form for an application, comprising: providing protein molecules having a molecular weight of at least about 25,000 Daltons; forming said protein molecules into microparticles; formulating said microparticles for administering said microparticles as a composition; and administering said formulation to an individual, wherein said microparticles are capable of being injected in less than about two minutes with a clinically acceptable amount of force.

47. The method of claim 46 wherein said formulating provides said protein molecules in said composition at a concentration of at least about 50 mg/ml.

48. The method of claim 46 wherein said formulating provides said protein molecules in said composition at a concentration of at least about 200 mg/ml.

49. The method of claim 46 wherein said formulating provides said protein molecules in said composition at a concentration of at least about 400 mg/ml.

50. The method of claim 46 wherein said formulating provides said protein molecules in said composition at a concentration of at least about 500 mg/ml.

51. The composition of claim 40 wherein said protein is insulin.

52. The method of claim 24 wherein said administering injects said composition in less than about two minutes with a clinically acceptable amount of force.

53. The method of claim 24 wherein said administering injects at least one ml of the composition in about 45 seconds or less with a clinically acceptable amount of force.

54. The method of claim 24 where said formulating prepares the composition for subcutaneous delivery, and said administrating is carried out subcutaneously.

55. The method of claim 24 wherein said administering is of a non-soluble microparticle form of said protein molecules, and said protein molecules are not endocytosed by cells of the immune system of the individual.

* * * * *